United States Patent
Pan et al.

(10) Patent No.: US 7,245,755 B1
(45) Date of Patent: Jul. 17, 2007

(54) ALGORITHM FOR IMAGE RECONSTRUCTION AND IMAGE NOISE ANALYSIS IN COMPUTED TOMOGRAPHY

(76) Inventors: Xiaochuan Pan, 1401 E. 54th St., Chicago, IL (US) 60615; Lifeng Yu, 5326 1/2 Drexel, #2, Chicago, IL (US) 60615; Chien-Min Kao, 509 1/2 Ridge Rd., Wilmette, IL (US) 60091

( * ) Notice: Subject to any disclaimer, the term of this patent is extended or adjusted under 35 U.S.C. 154(b) by 668 days.

(21) Appl. No.: 10/616,671

(22) Filed: Jul. 10, 2003

Related U.S. Application Data

(60) Provisional application No. 60/394,961, filed on Jul. 10, 2002.

(51) Int. Cl.
*G06K 9/00* (2006.01)
(52) U.S. Cl. .......................... 382/131; 378/4
(58) Field of Classification Search ........ 382/131–132, 382/154, 260, 280; 378/4–15, 17, 19
See application file for complete search history.

(56) References Cited

U.S. PATENT DOCUMENTS

| | | | | |
|---|---|---|---|---|
| 5,406,479 A | * | 4/1995 | Harman | 378/7 |
| 6,115,446 A | * | 9/2000 | Pan | 378/4 |
| 6,324,242 B1 | * | 11/2001 | Pan | 378/4 |
| 6,415,012 B1 | * | 7/2002 | Taguchi et al. | 378/15 |

OTHER PUBLICATIONS

Defrise "A Cone-beam reconstruction algorithm using shift variant filtering and cone-beam backprojection", IEEE, pp. 186-195, 1994.*
Bonnet, et al "Multiresolution Reconstruction in Fan-Beam-Tomography", IEEE, pp. 105-109, 2001.*

* cited by examiner

*Primary Examiner*—Daniel Mariam
(74) *Attorney, Agent, or Firm*—Welsh & Katz, Ltd.

(57) ABSTRACT

A method and apparatus are provided for reconstructing a tomographic image from fan-beam or cone-beam data. The method includes the steps of collecting fan-beam or cone-beam data over an image space, converting the fan-beam or cone-beam data to parallel-beam data with respect to a rotation angle within the image space, performing a shift variant filtration of the parallel-beam data within the image space and converting the processed data to images through backprojection or other means.

44 Claims, 20 Drawing Sheets

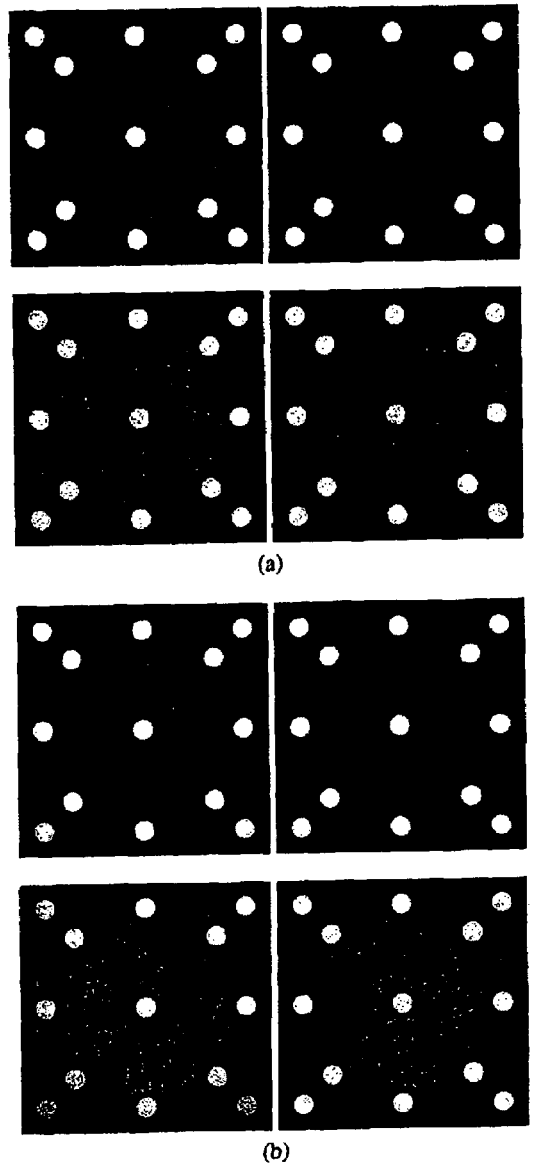
Figure 10 Images of the bead phantom reconstructed by use of the half-scan FFBP algorithm (left column) and the proposed algorithm (right column) from noiseless (upper row) and noisy (lower row) half-scan data generated with fan-beam configuration (a): $F = 850$ mm, $\gamma_{max} = 0.09\pi$ and configuration (b): $F = 250$ mm, $\gamma_{max} = 0.34\pi$, respectively. A display window [-1000HU, 1000HU] was used.

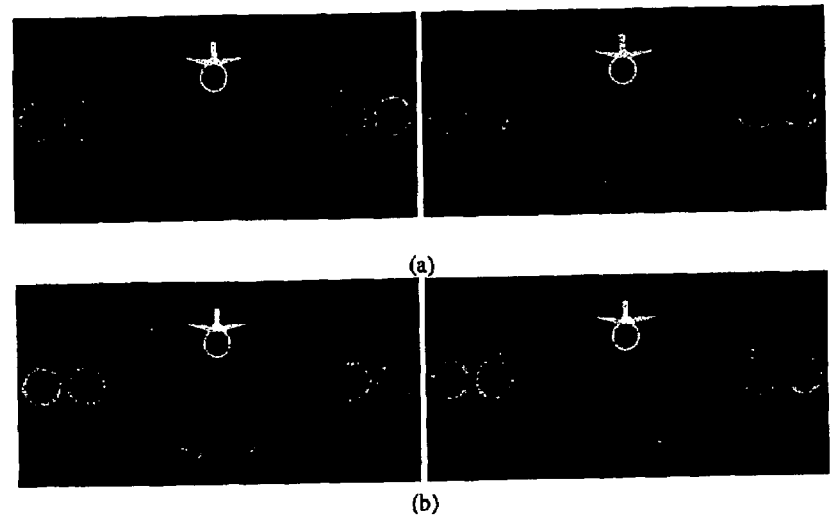

Figure 11: Images of the Thorax/Shoulder phantom reconstructed by use of the half-scan FFBP algorithm (left column) and the proposed half-scan algorithm (right column) from noisy half-scan data generated with fan-beam configuration (a): $F = 850$ mm, $\gamma_{max} = 0.09\pi$ and configuration (b): $F = 250$ mm, $\gamma_{max} = 0.34\pi$, respectively. A display window [-1000HU, 1000HU] was used.

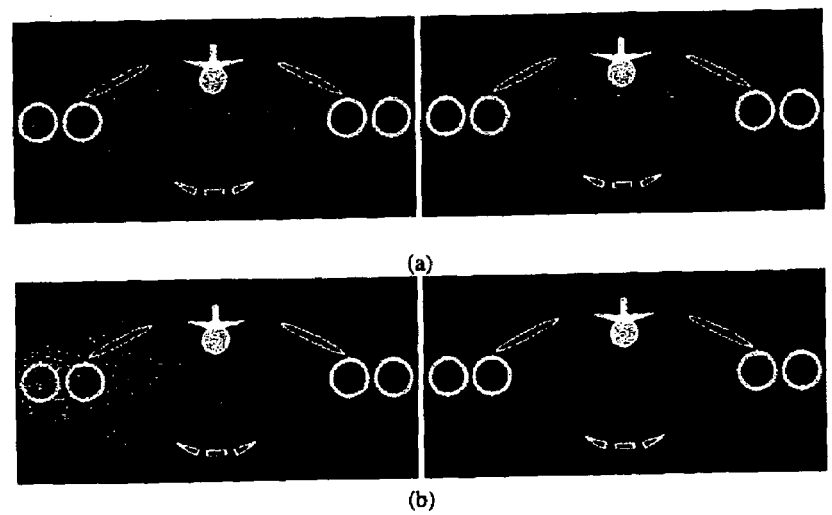

Figure 12: Same images as those in Fig. 3, but displayed with a grayscale window [-100HU, 200HU].

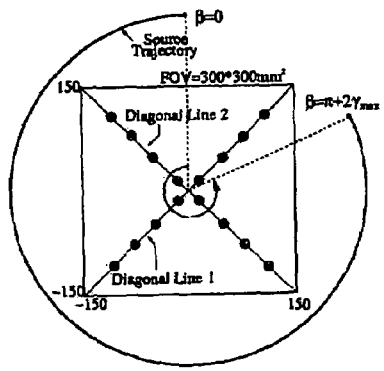
Figure 13 Locations at which the resolution properties of the two algorithms are evaluated.
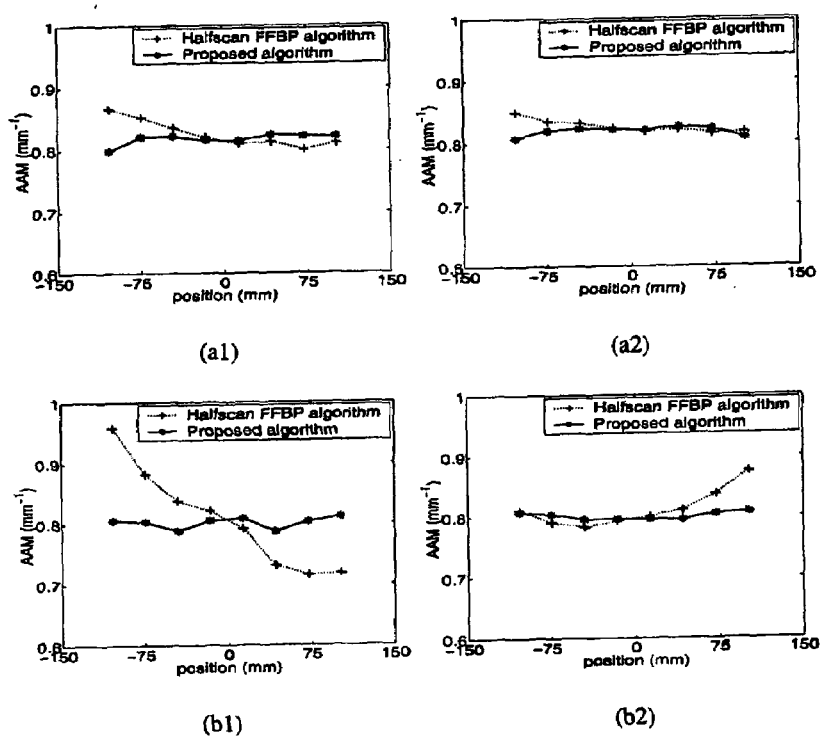
Figure 14: Panels (a1), (a2) and panels (b1), (b2) display the AAMs on diagonal lines 1 and 2, as shown in Fig. 5, obtained for configurations (a) and (b), respectively. It can be seen that the AAMs of the proposed half-scan algorithm are much more uniform than those of the half-scan FFBP algorithm.

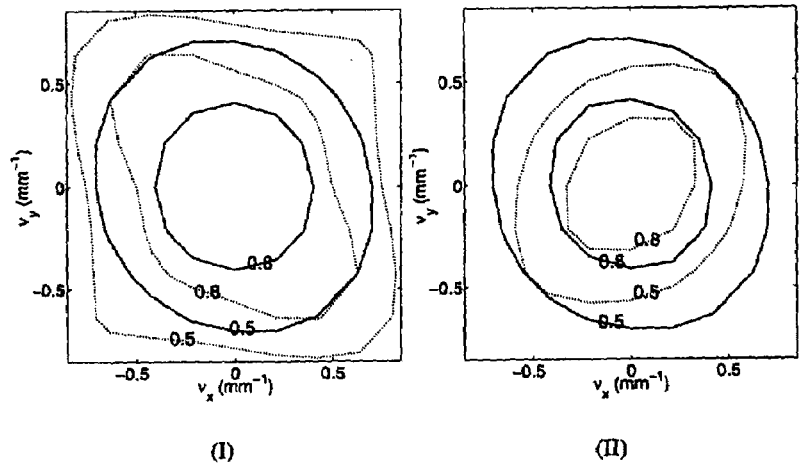

Figure 15: Contour plots of the Fourier transform moduli of the reconstructed point-like structures at (I) (-102mm, -102mm) and (II) (102mm, 102mm) for fan-beam configuration (b) obtained with the half-scan FFBP algorithm (dotted curves) and the proposed half-scan algorithm (solid curves). The highly non-circular contour shapes obtained with the half-scan FFBP algorithm indicate that the half-scan FFBP algorithm yields images with more significant distortions than does the proposed algorithm.

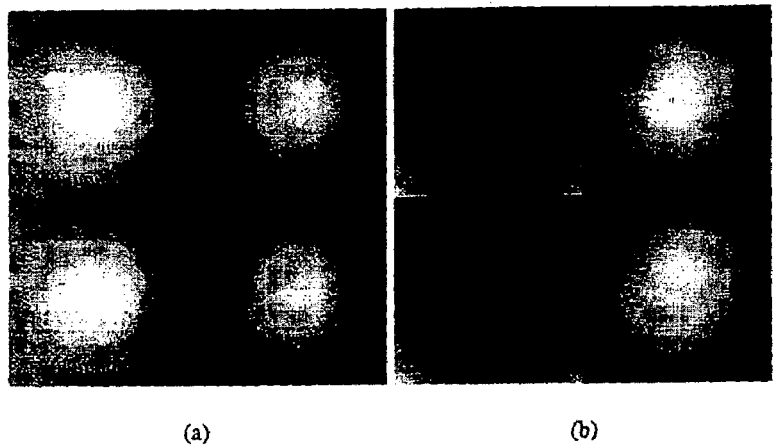

Figure 16: Image-variances obtained with the half-scan FFBP algorithm (left column) and the proposed half-scan algorithm (right column) for configuration (a) and (b), respectively. The theoretical and empirical results are shown in the top and bottom rows, respectively.

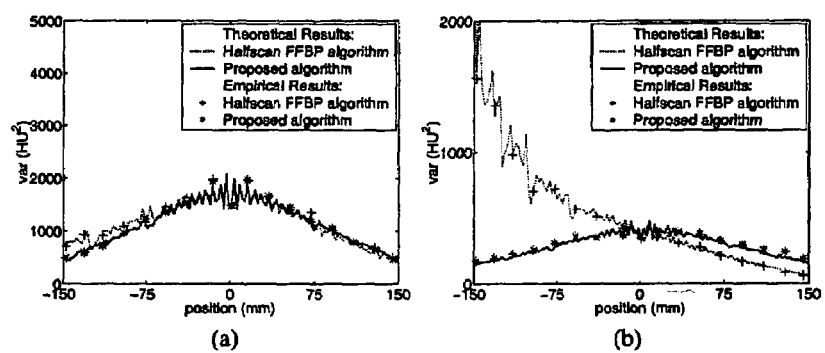
Figure 17 Theoretical profiles along the central-horizontal rows in image-variances obtained with the half-scan FFBP algorithm (the dotted curve) and the proposed half-scan algorithm (the solid curve) for configurations (a) and (b), respectively. Empirical results obtained with the half-scan FFBP algorithm (+) and the proposed half-scan algorithm (∗) are also displayed.

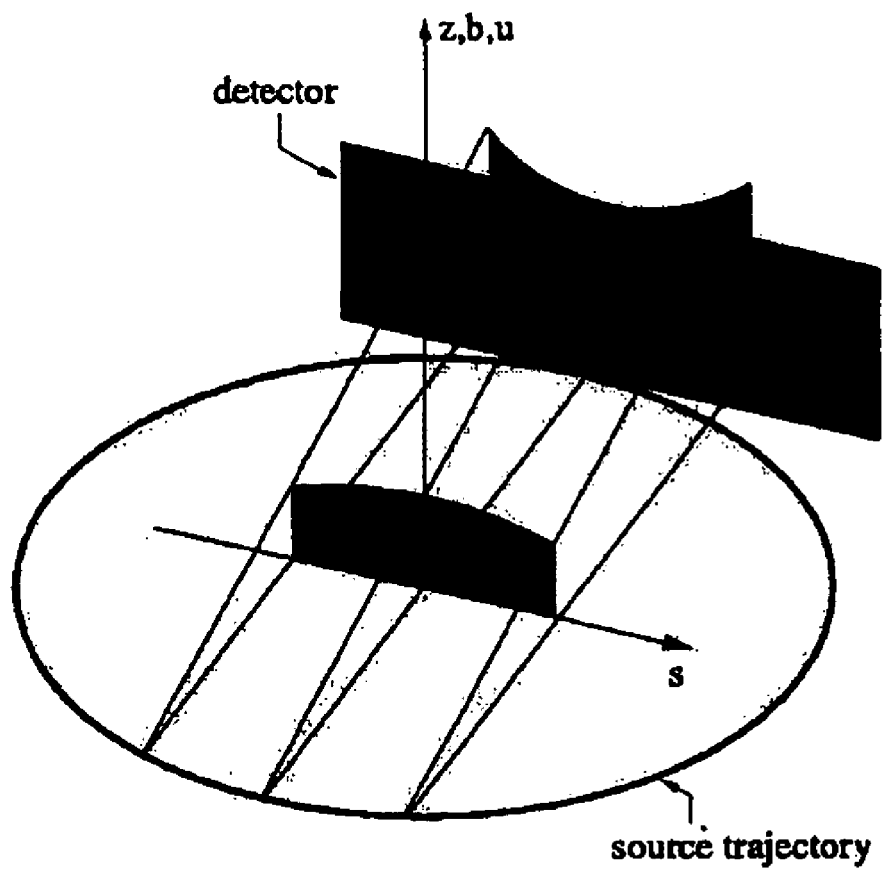
Figure 18: Vertically-parallel fan-beam data that are obtained by rebinning the cone-beam data acquired with a circular orbit.

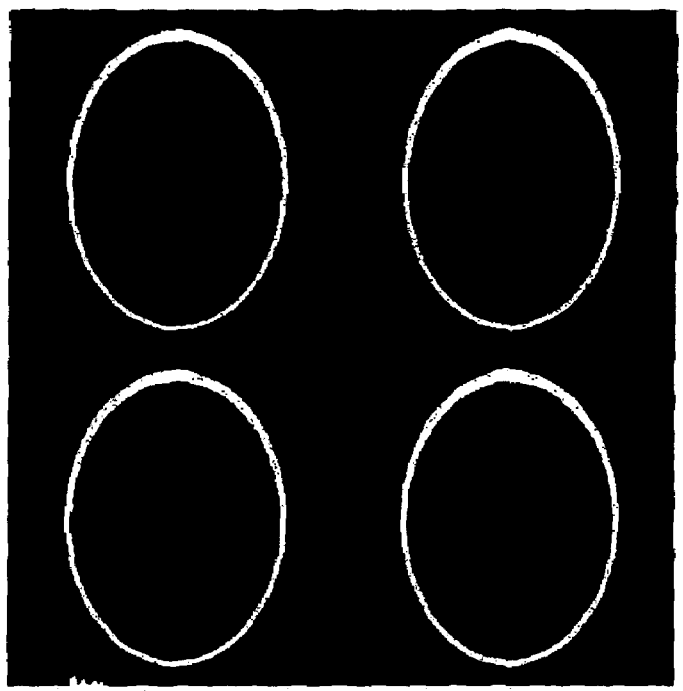

Figure 19 Images for a slice at $y = -37.5$ mm in the Shepp-Logan phantom by use of the FDK algorithm (upper left), the T-FDK algorithm (upper right), the proposed algorithm (lower left), and the proposed algorithm without cone-angle weighting (lower right), respectively. All images are showed in a gray-scale window [0, 60HU].

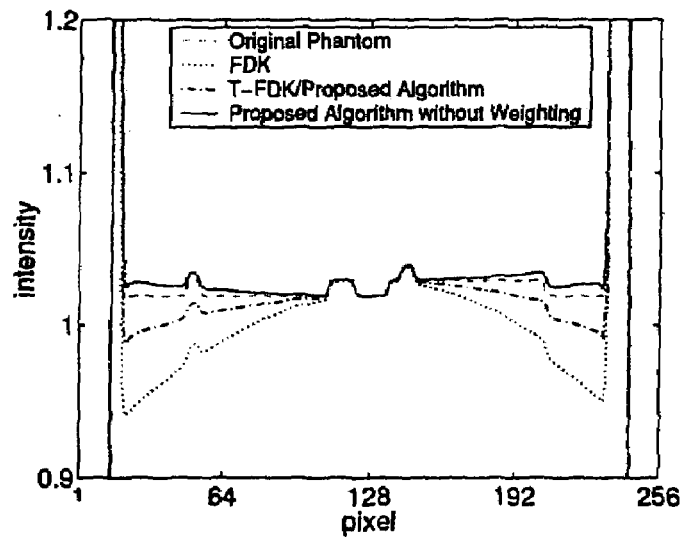

Figure 20 Profiles along an axis parallel to the $z$-axis with $x = 0$ mm, $y = -37.5$ mm in the reconstructed 3D Shepp-Logan images by use of the FDK algorithm (dotted), the T-FDK algorithm (dash-dotted), the proposed algorithm (overlapping with that of the T-FDK algorithm), and the proposed algorithm without cone-angle weighting (solid). The profile of the original phantom at the same position is drawn in dashed curve.

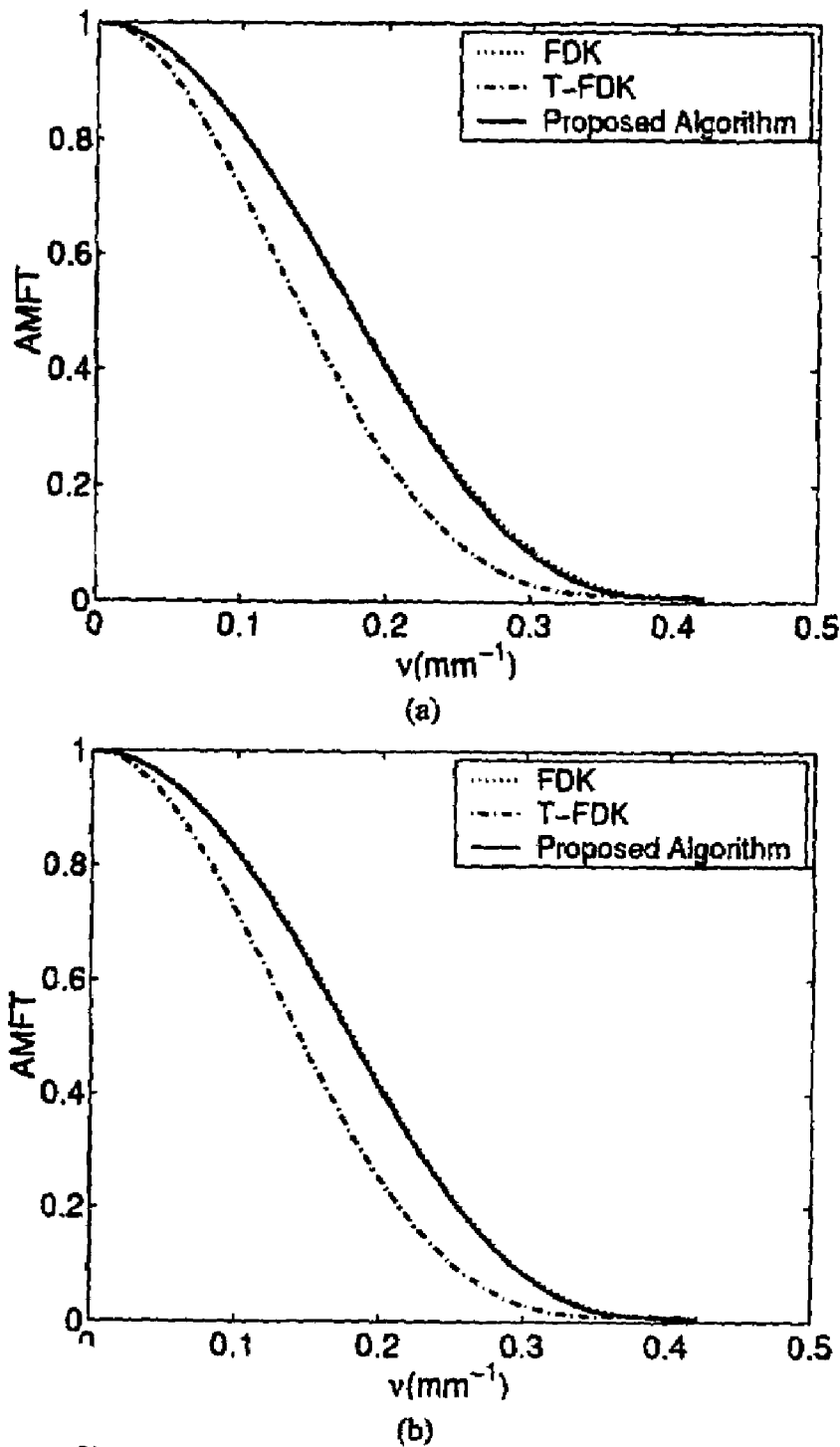
Figure 21: The AMFTs obtained for 2D images at (a) $z = 0$ mm and (b) $z = 37.5$ mm. The dotted, dashed, and the solid curves were obtained by use of the FDK algorithm, the T-FDK algorithm, and the proposed algorithm, respectively.

Figure 22: 2D variance-images obtained by use of the FDK algorithm (left column), the T-FDK algorithm (middle column), and the proposed algorithm (right column) at $z = 0$ mm (first row) and $z = 37.5$ mm (second row), respectively.

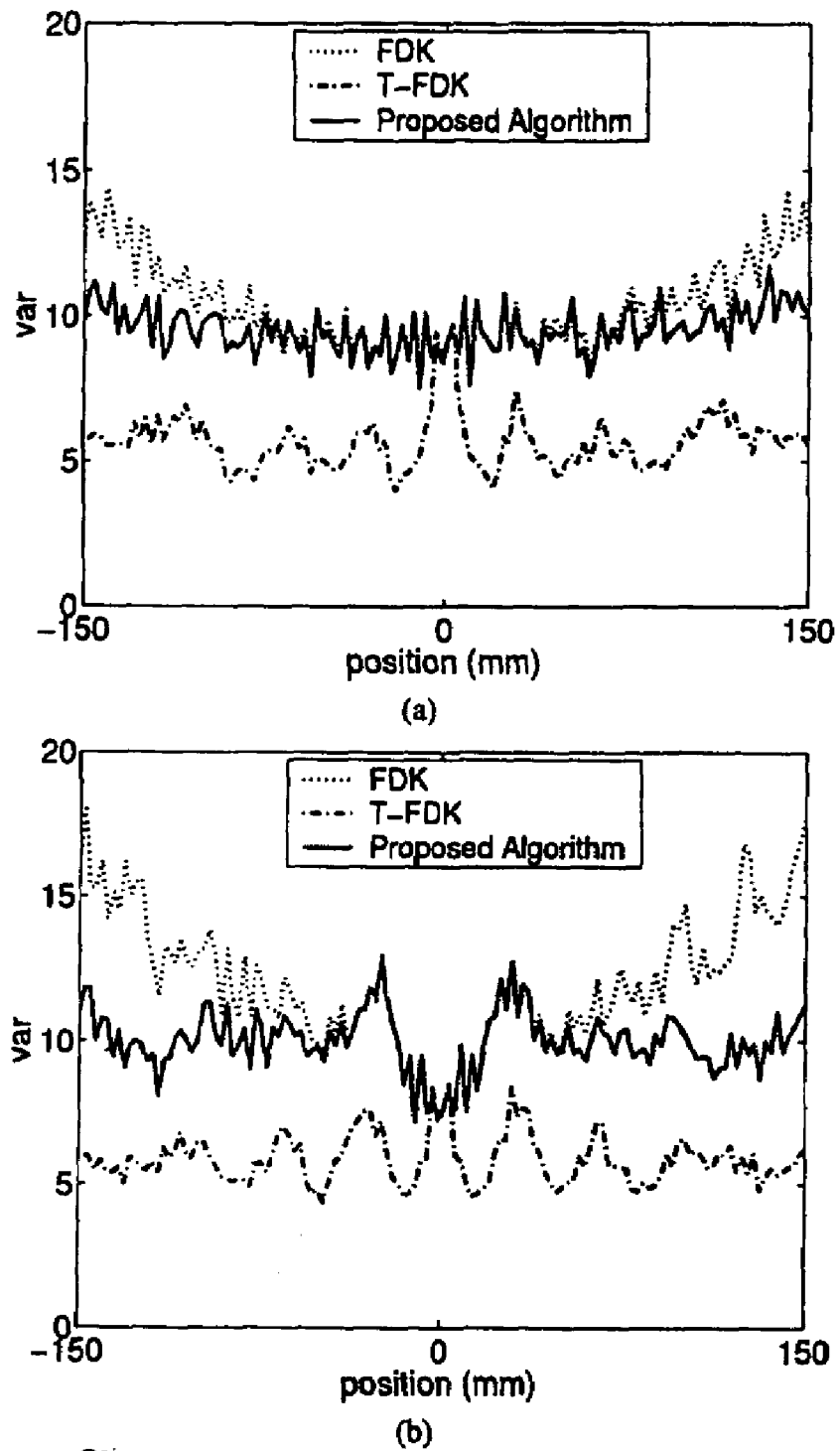
Figure 23 Profiles along the center columns in 2D variance-images in Fig22 at (a) $z = 0$ mm and (b) $z = 37.5$ mm, respectively. The dotted curve, the dashed curve, and the solid curve were obtained by use of the FDK algorithm, the T-FDK algorithm, and the proposed algorithm, respectively.

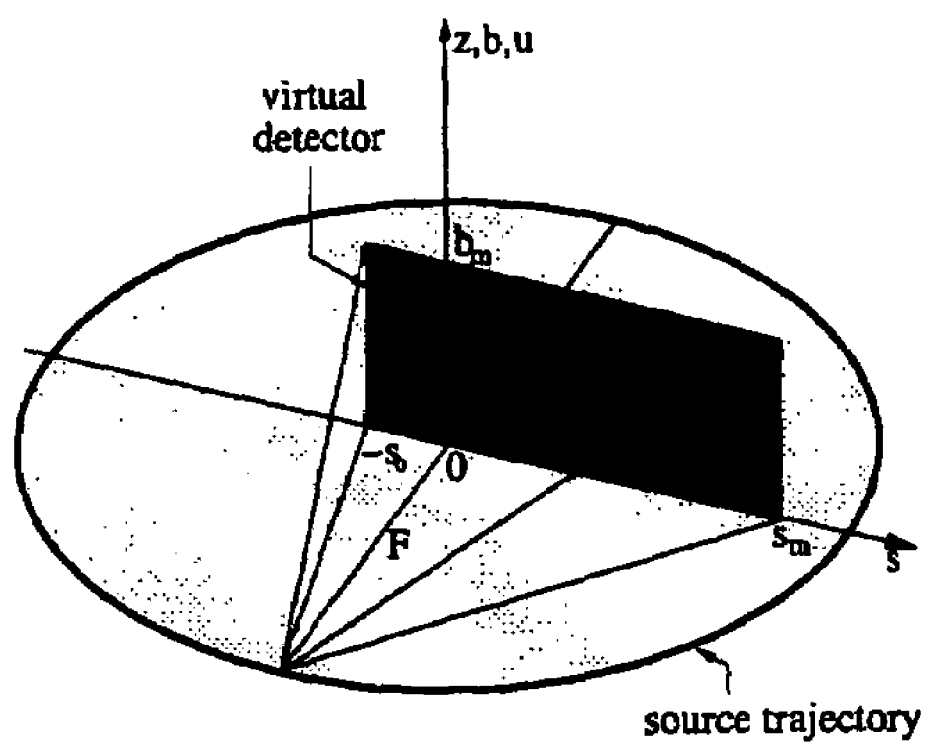
Figure 24 Asymmetric cone-beam CT configuration.

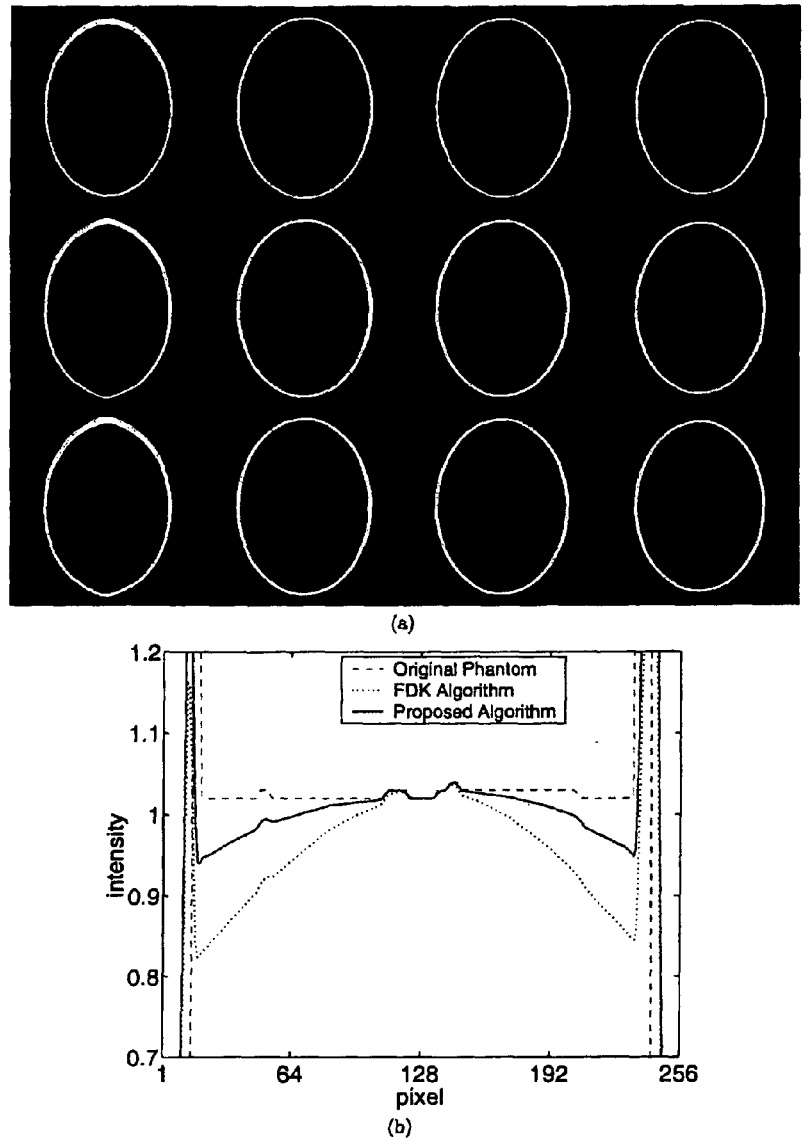

Figure 25 (a) Images for slices at $y = -37.5$ mm (first column), $z = 0$ mm (second column), $z = 18.8$ mm (third column), and $z = 37.5$ mm (forth column) in the 3D Shepp-Logan phantom. The first, second, and third rows show the corresponding slices in the original phantom, the images reconstructed by the FDK algorithm, the images reconstructed by the proposed algorithm, respectively. (b) Profiles along the center column ($z$ direction) of the images in first column of (a).

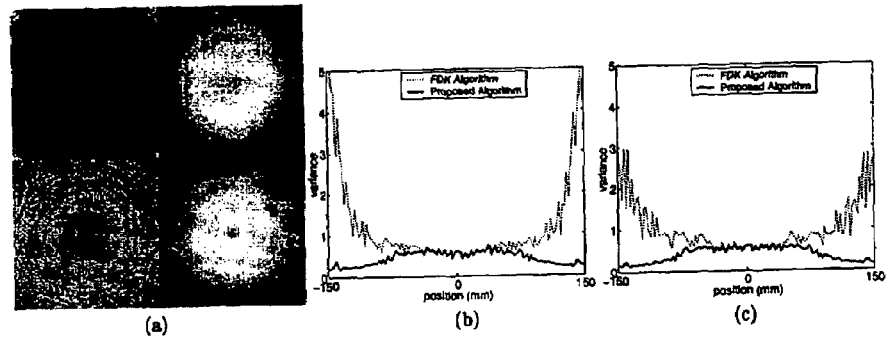

Figure 26 (a) 2D variance-images at $z = 0$ mm (upper row) and $z = 37.5$ mm (lower row) obtained by use of the FDK algorithm (left column) and the proposed algorithm (right column). (b-c)Profiles along the diagonal lines of the variance-images in the first and second rows of (a).

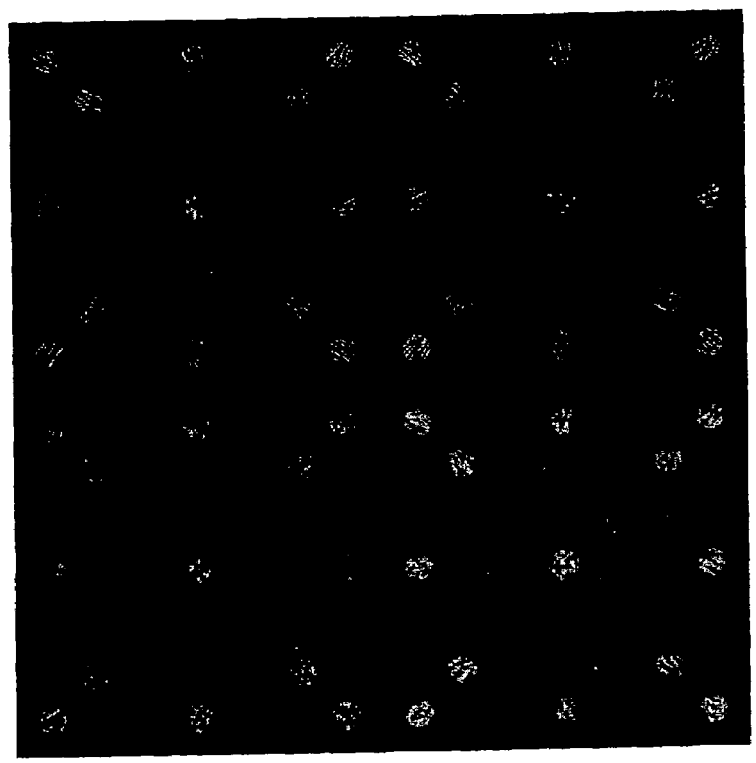

Figure 27 Reconstructed images by use of the FDK algorithm (upper row) and the proposed algorithm (lower row) for 2D slices at $z = 0$ mm (left column) and $z = 37.5$ mm (right column) from noisy data generated with the asymmetric cone-beam configurations.

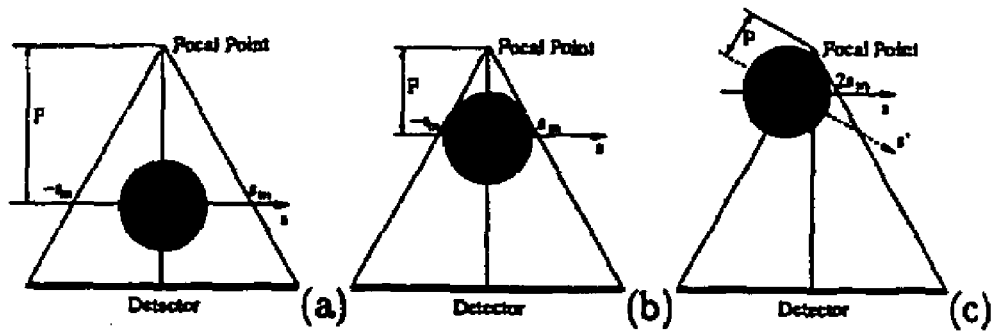
Fig. 28 Fan-beam configuration with a fixed maximum fan-angle that is determined by the size of the detector and its distance to the focal spot. (a) and (b) show configurations in which the center of a given FOV (i.e, the object) is placed at different distances from the focal spot. (c) displays the asymmetric scanning configuration.

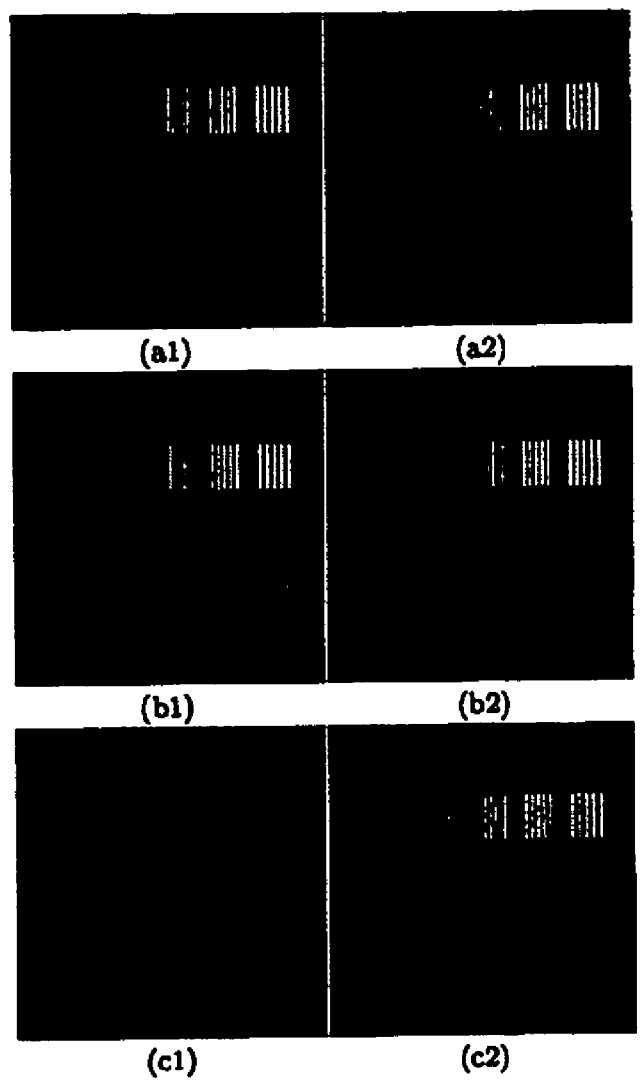
Fig. 29 Images reconstructed with the FFBP algorithm (1) and the proposed algorithm (2) for the three configurations (a), (b), and (c) shown in Fig. 1.
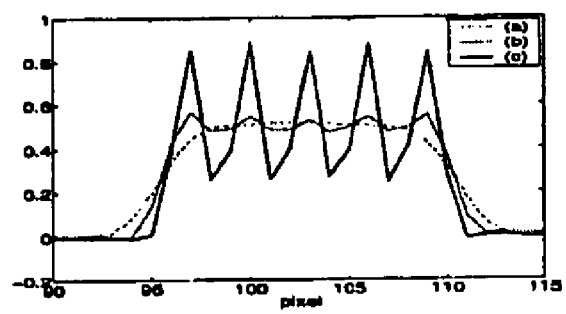
Fig. 30 Profiles of the finest bar pattern in Fig. 2(a2), (b2), and (c2).

ALGORITHM FOR IMAGE RECONSTRUCTION AND IMAGE NOISE ANALYSIS IN COMPUTED TOMOGRAPHY

The U.S. Government has a paid-up license in this invention and the right in limited circumstances to require the patent owner to license others on reasonable terms as provided for by the terms of Grant No. EB00225 and CA70449 awarded by the National Institutes of Health.

FIELD OF THE INVENTION

The field of the invention relates to computed tomograpy and more particularly to methods of reconstructing images.

BACKGROUND OF THE INVENTION

In computed tomography (CT), the fan-beam filtered backprojection (FFBP) algorithm is typically used for reconstruction of images directly from fan-beam data. In single- and multi-slice helical CT, the FFBP algorithm may also be used for reconstructing multiple slices of two-dimensional (2D) images from fan-beam data that are converted from measured helical data. The FDK algorithm may be used for cone-beam data. It has been known that the spatially variant weighting factor in the FFBP algorithm can significantly amplify data noise and sample aliasing in situations where the focal lengths are comparable to or smaller than the size of the field of view (FOV). One previously developed hybrid algorithm reconstructs images from parallel-beam data that are converted from the acquired fan-beam data. Because the previous hybrid algorithm involves no weighting factor similar to that in the FFBP algorithm, it is generally less susceptible to data noise and sample aliasing and is computationally more efficient than is the FFBP algorithm. However, because the previous hybrid algorithm invokes an explicit one-dimensional (1D) interpolation for converting fan-beam projections to parallel-beam projections along the radial direction, it can lead to reduced image resolution when fan-beam samples along the radial direction are sparse.

A new hybrid algorithm is described herein that retains the favorable resolution property of the FFBP algorithm and the favorable noise property of the previous hybrid algorithm while eliminating their shortcomings. Analytic formulas are also derived for evaluating variances in images reconstructed by use of the FFBP, the previous hybrid, and the new hybrid algorithms in their discrete forms. Such theoretical formulas not only may provide insights into the algorithms' precision in estimation tasks, but also may be used for assessing their performance by use of mathematical model observers in detection/classification tasks. Computer-simulation studies for quantitative evaluation of resolution and noise properties of these algorithms are provided. Using moduli of Fourier transforms of reconstructed images, image-resolution properties may be compared and possible distortions identified. From a large number of reconstructed noisy images, empirical image variances are computed and compared with the derived theoretical formulas. Numerical results of these simulation studies confirm that the proposed new hybrid algorithm combines the favorable resolution property of the FFBP algorithm and the noise property of the previous hybrid algorithm while eliminating their shortcomings. Empirical image variances also validate the novel theoretical formulas for image variances. The analysis contained herein has also been extended to half-scan CT, cone beam CT, asymmetric scanning and high resolution scanning techniques.

SUMMARY

A method and apparatus are provided for reconstructing a tomographic image from fan-beam or cone-beam data. The method includes the steps of collecting fan-beam or cone-beam data over an image space, converting the cone-beam data to parallel fan-beam data or the fan-beam data to parallel-beam data with respect to a rotation angle within the image space, performing a shift variant filtration of the parallel-beam data or parallel fan-beam data within the image space and converting the processed data to images through backprojection or other means.

BRIEF DESCRIPTION OF THE DRAWINGS

FIG. 10 depicts images of a bead phantom that may be generated by the system of FIG. 1;

FIG. 11 depicts images of a thorax/shoulder phantom that may be generated by the system of FIG. 1;

FIG. 12 depicts the images of FIG. 11 through a grayscale window

FIG. 13 depicts locations at which the resolution properties of two algorithms used by the system of FIG. 1 may be evaluated;

FIG. 14 depicts AAMs that may be used by the system of FIG. 1;

FIG. 15 depicts contour plots that may be generated by the system of FIG. 1;

FIG. 16 depicts image variances that may be generated by the system of FIG. 1;

FIG. 17 depicts theoretical profiles that may be generated by the system of FIG. 1;

FIG. 18 depicts a vertically-parallel fan beam data that may be generated by the system of FIG. 1;

FIG. 19 depicts images that may be generated by the system of FIG. 1 for a Shepp-Logan phantom;

FIG. 20 depicts comparative profiles that may be generated by the system of FIG. 1 using Shepp-Logan information;

FIG. 21 depicts AMFTs that may be generated by the system of FIG. 1;

FIG. 22 depicts 2D variance images that may be generated by the system of FIG. 1;

FIG. 23 depicts profiles along the center columns in 2D variance-images that may be generated by the system of FIG. 1;

FIG. 24 depicts asymmetric cone-beam configuration information that may be used by the system of FIG. 1;

FIG. 25 depicts images that may be generated by the system of FIG. 1 using a Shepp-Logan phantom;

FIG. 26 depicts variance-images that may be generated by the system of FIG. 1;

FIG. 27 depicts reconstructed images generated by the system of FIG. 1 using asymmetric cone-beam configurations;

FIG. 28 depicts fan-beam configuration that may be used by the system of FIG. 1;

FIG. 29 depicts comparative images that may be generated by the system of FIG. 1; and FIG. 30 depicts bar pattern profiles that may be generated by the system of FIG. 1.

DETAILED DESCRIPTION OF AN ILLUSTRATED EMBODIMENT

Figure 3:
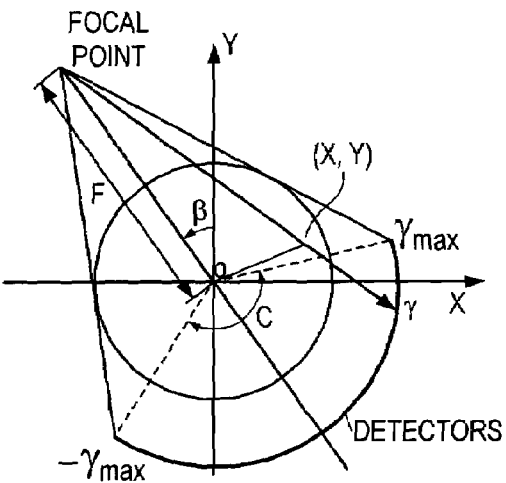
FIG. 3 depicts fan-beam geometry that may be used by the system of FIG. 1.

In this description, mathematical notations are used that characterize the fan-beam geometry in a typical CT scanner. As shown in FIG. 3, a continuous fan-beam projection $q(\gamma,\beta)$ is acquired at a view angle $\beta$. The collection of $q(\gamma,\beta)$ for $|\gamma| \leq \gamma_{max}$ and $\beta \in [0, 2\pi)$ is referred to as the continuous fan-beam sinogram, where $\gamma_{max}$ is defined in FIG. 3. The format followed herein will be to first summarize the FFBP and the previous hybrid algorithm in their continuous and discrete forms. Following the summary of FFBP and previous hybrid algorithm, the new hybrid algorithm will be discussed.

The well-known FFBP algorithm that reconstructs an image directly from a fan-beam sinogram $q(\gamma,\beta)$ is given by $$a(x, y) = \frac{1}{2}\int_0^{2\pi} d\beta \frac{F}{L^2} \int_{-\gamma_{max}}^{\gamma_{max}} d\gamma \cos\gamma\, q(\gamma, \beta) \left[\frac{\gamma'_0 - \gamma}{\sin(\gamma'_0 - \gamma)}\right]^2 h(\gamma'_0 - \gamma), \quad (1)$$

where the constant F denotes the known focal length, $2\gamma_{max}$ is the maximum fan angle, h is the spatial domain representation of the ramp filter, and L and $\gamma'_o$ are functions of the image-space coordinates x and y and the projection angle $\beta$, which are given by $$L(x,y,\beta) = [F^2 + x^2 + y^2 + 2F(x\sin\beta - y\cos\beta)]^{1/2} \text{ and}$$

$$\gamma'_0(x, y, \beta) = \arctan\left[\frac{x\cos\beta + y\sin\beta}{F + x\sin\beta - y\cos\beta}\right]. \quad (2)$$

It has been demonstrated that the factor L can significantly amplify noise and aliasing artifacts in images reconstructed from data acquired with configurations of small focal lengths and/or a large maximum fan angle.

One prior art hybrid algorithm may be described in a continuous form as follows. Let $p(\xi,\phi)$ denote a continuous parallel-beam sinogram, which, in the absence of data noise, is identical to the corresponding fan-beam sinogram provided that $$\xi = F\sin\gamma \text{ and } \phi = \beta + \gamma. \quad (3)$$

This observation implies that the parallel-beam sinogram can be obtained from the corresponding fan-beam sinogram. Let $Q_m(\gamma)$ denote the Fourier series expansion of the fan-beam sinogram $q(\gamma,\beta)$ with respect to $\beta$. The previous hybrid algorithm first calculates the parallel-beam sinogram from $Q_m(\gamma)$ (i.e., from the fan-beam sinogram $q(\gamma,\beta)$) as $$p(\xi, \phi) = q'(\gamma, \phi) = \frac{1}{2}\sum_{m=-\infty}^{\infty} [e^{-jm\gamma}Q_m(\gamma) + (-1)^m e^{jm\gamma}Q_m(-\gamma)]e^{jm\phi} \quad (4)$$

and then reconstructs an image from the computed parallel-beam sinogram by use of the parallel-beam filtered back-projection algorithm as $$a(x, y) = \frac{1}{2}\int_0^{2\pi} d\phi \int_{-\infty}^{\infty} d\xi\, p(\xi, \phi) h(\xi_0 - \xi), \quad (5)$$

where $$\xi_0(x,y,\phi) = x\cos\phi + y\sin\phi. \quad (6)$$

Figure 1:
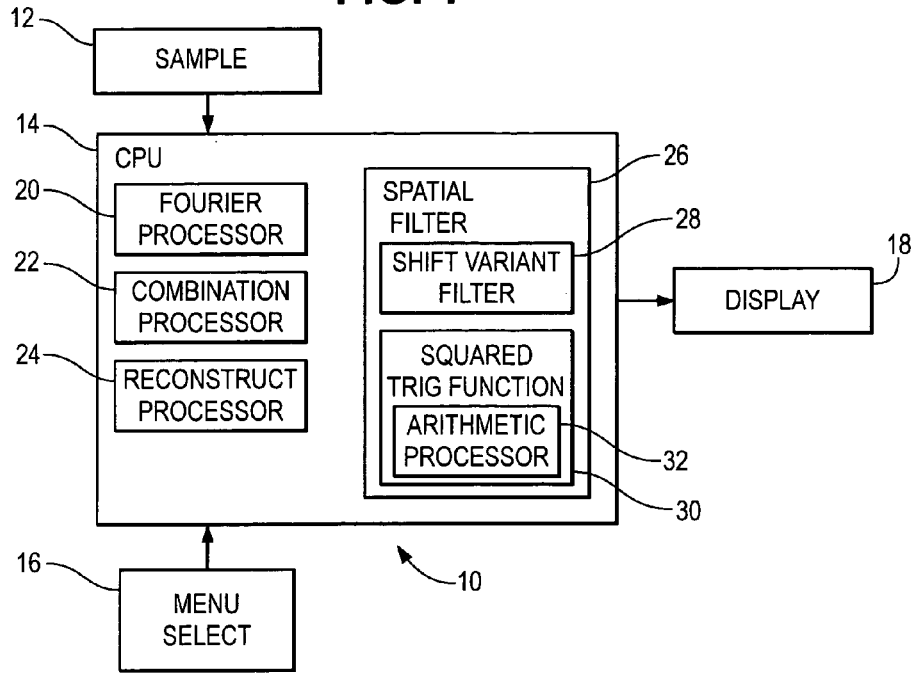
FIG. 1 depicts a tomographic image reconstruction system in accordance with an illustrated embodiment of the invention.

The new hybrid algorithm will be considered next. FIG. 1 depicts a system 10 that may be used with the new hybrid algorithm in accordance with an illustrated embodiment of the invention. As shown in Eq. (18) below, the previous hybrid algorithm invokes a 1D interpolation along $\gamma$ for estimating the discrete parallel-beam sinogram on uniform grids along $\xi$. Such a 1D interpolation may result in reduced image resolution in situations where fan-beam samples along $\gamma$ are sparse. Below, a new hybrid algorithm is described that can avoid such a 1D explicit interpolation and thus retain the resolution property of the FFBP algorithm.

Using Eqs. (3) and (6), one can define the quantity $\gamma_0(x,y,\phi)$ as follows $$\gamma_0(x, y, \phi) = \arcsin\left[\frac{\xi_0(x, y, \phi)}{F}\right]. \quad (7)$$

Substituting this definition and $q'(\gamma,\phi)$ into Eq. (5) yields $$a(x, y) = \frac{F}{2}\int_0^{2\pi} d\phi \int_{-\gamma_{max}}^{\gamma_{max}} d\gamma \cos\gamma\, q'(\gamma, \phi) h(F\sin\gamma_0 - F\sin\gamma), \quad (8)$$

where $q'(\gamma,\phi)$ is given in Eq. (4), and $$h(F\sin\gamma_0 - F\sin\gamma) = \int_{-\infty}^{\infty} d\nu\, |\nu| e^{j2\pi\nu F(\sin\gamma_0 - \sin\gamma)} \quad (9)$$

We now define a new frequency variable as $\nu' = \nu F(\sin\gamma_0 - \sin\gamma)/(\gamma_0 - \gamma)$. Using $\nu'$ in Eq. (9) yields $$h(F\sin\gamma_0 - F\sin\gamma) = \frac{1}{F^2}\left[\frac{\gamma_0 - \gamma}{\sin\gamma_0 - \sin\gamma}\right]^2 \int_{-\infty}^{\infty} d\nu'\, |\nu'| e^{j2\pi\nu'(\gamma_0 - \gamma)} \quad (10)$$

$$= \frac{1}{F^2}\left[\frac{\gamma_0 - \gamma}{\sin\gamma_0 - \sin\gamma}\right]^2$$

-continued $$= \left[\frac{\cos\frac{\gamma_0 - \gamma}{2}}{\cos\frac{\gamma_0 + \gamma}{2}}\right]^2 h(\gamma_0 - \gamma).$$

Substituting Eq. (10) into Eq. (8), we obtain the new hybrid algorithm as $$a(x, y) = \qquad (11)$$

$$\frac{1}{2F}\int_0^{2\pi} d\phi \int_{-\gamma_{max}}^{\gamma_{max}} d\gamma \cos\gamma q'(\gamma, \phi)\left[\frac{\gamma_0 - \gamma}{\sin(\gamma_0 - \gamma)}\right]^2 h(\gamma_0 - \gamma)g(\gamma_0, \gamma),$$

where $$g(\gamma_0, \gamma) = \left[\frac{\cos\frac{\gamma_0 - \gamma}{2}}{\cos\frac{\gamma_0 + \gamma}{2}}\right]^2 \qquad (12)$$

Inspection of Eqs. (1) and (11) indicates that the function $g(\gamma_0,\gamma)$ changes the shift-invariant filtration in the FFBP algorithm into a shift-variant filtration in the new hybrid algorithm (see the integrations over $\gamma$ in Eqs. (1) and (11)). However, because the new hybrid algorithm does not involve a factor similar to the L factor (see Eq. (2)) in the FFBP algorithm, it is hypothsized that the new hybrid algorithm amplifies noise and aliasing artifacts less significantly than does the FFBP algorithm when the focal length F is comparable to or smaller than the FOV size. This hypothesis is quantitatively verified in numerical studies below.

Figure 2:
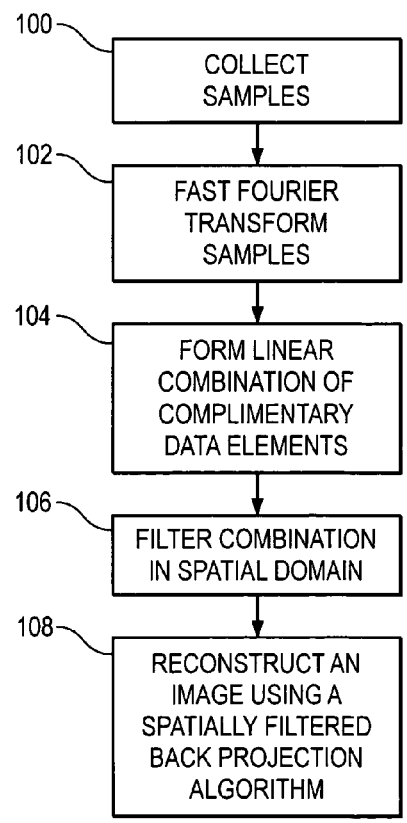
FIG. 2 depicts a flow chart of process steps that may be used by the system of FIG. 1.

Equations 7-12 provide the basis of the new and novel algorithm used by the system 10 of FIG. 1. FIG. 2 is a flow chart of process steps that may be used by the system 10 of FIG. 1.

In general, a sampling system 12 may collect fan-beam samples conventionally. A menu graphical user interface 16 may be used to enter values and to provide the overall control of the system 10. A display 18 may be used to display the images provided by the system 10.

Once collected, a fast Fourier processor 20 performs a fast Fourier transform on the collected data within a Fourier processor 20. Once transformed, a linear combination of complementary data elements may be formed from the transformed data within a combination processor 22 as described in U.S. Pat. No. 6,115,466 by the inventor of the instant application (incorporated herein by reference).

Following formation of the linear combination of data elements, the linear combination may be filtered in the spatial domain by a spatial filter 26. Filtering in that spatial domain may be accomplished with the use of a shift variant filter 28. The variation in the filtering function may be accomplished using a squared trigonometric function 30 as shown in Eq. 12 in combination with the arithmetic processor.

The reconstruction algorithms in discrete forms may be considered next. The FFBP, the previous hybrid, and the new hybrid algorithms in their continuous forms (i.e., Eqs. (1), (5), and (11)) are mathematically equivalent, but only in their continuous forms. It can be shown that the noise properties in images reconstructed by use of these algorithms in their continuous forms are also identical. In reality, one can reconstruct images by use of algorithms only in their discrete forms. Because the FFBP and hybrid algorithms in their discrete forms propagate data noise and/or aliasing artifacts differently, they reconstruct images with different noise (and/or aliasing) properties. The FFBP and hybrid algorithms may be derived in their discrete forms and used to study the noise and aliasing properties in reconstructed images. Throughout this description I+1 and N+1 may be used to denote the number of detector bins at a projection view and the number of projection views, respectively. For notational convenience in expressing these reconstruction algorithms in their discrete forms, both I>0 and N>0 are assumed to be even integers. However, similar results can readily be derived for 1 and N being odd integers.

The FFBP algorithm in discrete form may be considered first. Let $$\Delta\gamma = \frac{2\gamma_{max}}{I+1}$$

and $\gamma_i = i\Delta\gamma$, where $i = -I/2, -I/2+1, \ldots, I/2-1, I/2$, let $$\Delta\beta = \frac{2\pi}{N+1}$$

and $\beta_n = n\Delta\beta$, where $n = 0, 1, \ldots, N$, and let $\{q(\gamma_i, \beta_n)\}$ denote samples of the fan-beam sinogram.

For a given point (x,y) in the image space and a projection angle $\beta$, one can calculate $$k = int\left[\frac{\gamma'_0(x, y, \beta_n)}{\Delta\gamma}\right] \qquad (13)$$

$$\eta(x, y, \beta_n) = \frac{\gamma'_0(x, y, \beta_n)}{\Delta\gamma} - k,$$

where the function "int [b]" yields the largest integer that is smaller than the number b, and $\gamma'_0(x,y,\beta_n)$ is given by Eq. (2). Therefore, the image $\alpha_F(x,y)$ reconstructed by use of the FFBP algorithm in its discrete form can be expressed as $$a_F(x, y) = \frac{\Delta\beta}{2}\sum_{n=0}^{N}\frac{F}{[L(x, y, \beta_n)]^2} \qquad (14)$$

$$\{[1 - \eta(x, y, \beta_n)]\bar{q}(\gamma_k, \beta_n) + \eta(x, y, \beta_n)\bar{q}(\gamma_{k+1}, \beta_n)\},$$

where $\bar{q}(\gamma_k,\beta_n)$ denotes the filtered discrete fan-beam sinogram, which is given by $$\bar{q}(\gamma_k, \beta_n) = \Delta\gamma\sum_{i=-I/2}^{I/2}\cos\gamma_i q(\gamma_i, \beta_n)H(k, i), \qquad (15)$$

and H denotes the filtration matrix with elements defined as $$H(k, i) = \left[\frac{\gamma_k - \gamma_i}{\sin(\gamma_k - \gamma_i)}\right]^2 h(\gamma_k - \gamma_i). \qquad (16)$$

It may be noted in passing that the two terms in the curly brackets of Eq. (15) (and in Eqs. (20) and (25) for the previous and new hybrid algorithms discussed below) indicate that a linear interpolation has been used in the back-projection step. One can readily use other interpolation schemes to replace the linear interpolation. However, such a change of interpolation schemes would result in no fundamental change of the theoretical derivation and results discussed herein.

The previous hybrid algorithm may be considered next in its discrete form. Let $$\Delta\xi = \frac{2F\sin\gamma_{max}}{I+1}$$

and $\xi_i = i\Delta\xi$, where $i = -I/2, -I/2+1, \ldots, I/2-1, I/2$, and let $$\Delta\phi = \frac{2\pi}{N+1}$$

and $\phi_n = n\Delta\phi$ where $n = 0, 1, \ldots, N$. Using Eq. (4), one can estimate the discrete parallel-beam sinogram $\hat{p}(\xi_i, \phi_n)$ sampled on uniform grids $\{\xi_i\}$. However, because of the non-linear relationship between $\xi$ and $\gamma$ (see Eq. (3)), uniform grids $\{\xi_i\}$ do not correspond to uniform grids $\{\gamma_i\}$ on which the fan-beam sinogram is sampled. For a given $\xi_i$ we define $$\alpha(\xi_i) = \arcsin\left(\frac{\xi_i}{F}\right) \qquad (17)$$

$$l = \text{int}\left[\frac{\alpha(\xi_i)}{\Delta\gamma}\right]$$

$$\lambda(\xi_i) = \frac{\alpha(\xi_i)}{\Delta\gamma} - l.$$

In the previous hybrid algorithm, the discrete parallel-beam sinogram $\hat{p}(\xi_i, \phi_n)$ on uniform grids $\{\xi_i\}$ is first estimated from the discrete fan-beam sinogram sampled on uniform grids $\{\gamma_i\}$ by invoking a 1D linear interpolation as $$\hat{p}(\xi_i, \phi_n) = (1 - \lambda(\xi_i))\hat{q}'(\gamma_l, \phi_n) + \lambda(\xi_i)\hat{q}'(\gamma_{l+1}, \phi_n), \qquad (18)$$

where, according to Eq. (4), $$\hat{q}'(\gamma_l, \phi_n) = \frac{1}{2}\sum_{m=-N/2}^{N/2}[e^{-jm\alpha(\xi_i)}Q'_m(\gamma_l) + (-1)^m e^{jm\alpha(\xi_i)}Q'_m(-\gamma_l)]e^{jm\phi_n} \qquad (19)$$

$$\hat{q}'(\gamma_{l+1}, \phi_n) =$$
$$\frac{1}{2}\sum_{m=-N/2}^{N/2}[e^{-jm\alpha(\xi_i)}Q'_m(\gamma_{l+1}) + (-1)^m e^{jm\alpha(\xi_i)}Q'_m(-\gamma_{l+1})]e^{jm\phi_n},$$

and $Q'_m(\gamma_i)$ denotes the discrete Fourier transform obtained from the discrete fan-beam sinogram $q(\gamma_i, \beta_n)$ with respect to $\beta_n$. Therefore, the image $\alpha_{PH}(x,y)$ reconstructed by use of the previous hybrid algorithm in its discrete form can be expressed as $$a_{PH}(x, y) = \qquad (20)$$

$$\frac{\Delta\phi}{2}\sum_{n=0}^{N}\{[1 - \zeta(x, y, \phi_n)]\overline{p}(\xi_k, \phi_n) + \zeta(x, y, \phi_n)\overline{p}(\xi_{k+1}, \phi_n)\},$$

where $$k = \text{int}\left[\frac{\xi_0(x, y, \phi_n)}{\Delta\xi}\right] \qquad (21)$$

$$\zeta(x, y, \phi_n) = \frac{\xi_0(x, y, \phi_n)}{\Delta\xi} - k,$$

$\xi_0(x, y, \phi_n)$ is given by Eq. (6), and $\overline{p}(\xi_k, \phi_n)$ denotes the filtered discrete parallel-beam sinogram, which is obtained from the interpolated discrete parallel-beam sinogram in Eq. (19) as $$\overline{p}(\xi_k, \phi_n) = \Delta\phi \sum_{i=-I/2}^{I/2} \hat{p}(\xi_i, \phi_n)h(\xi_k - \xi_i). \qquad (22)$$

The new hybrid algorithm may be considered next in its discrete form. Let $$\Delta\gamma = \frac{2\gamma_{max}}{I+1}$$

and $\gamma_i = i\Delta\gamma$, where $i = -I/2, -I/2+1, \ldots, I/2-1, I/2$, and let $$\Delta\phi = \frac{2\pi}{N+1}$$

and $\phi_n = n\Delta\phi$, where $n = 0, 1, \ldots, N$. For a given point $(x,y)$ in the image space and a projection angle $\phi_n$ one can calculate $$k = \text{int}\left[\frac{\gamma_0(x, y, \phi_n)}{\Delta\gamma}\right] \qquad (23)$$

$$\mu(x, y, \phi_n) = \frac{\gamma_0(x, y, \phi_n)}{\Delta\gamma} - k,$$

where $\gamma_0(x, y, \phi_n)$ is given by Eq. (7).

Based upon Eq. (4), a discrete version of the quantity $q'(\gamma, \phi)$ can be obtained as $$q'(\gamma_i, \phi_n) = \frac{1}{2}\sum_{m=-N/2}^{N/2}[e^{-jm\gamma_i}Q'_m(\gamma_i) + (-1)^m e^{jm\gamma_i}Q'_m(-\gamma_i)]e^{jm\phi_n}. \qquad (24)$$

Considering Eqs. (11) and (24), the image $\alpha_{NH}(x,y)$ reconstructed by use of the new hybrid algorithm in its discrete form can be expressed as $$a_{NH}(x, y) = \qquad (25)$$

$$\frac{\Delta\phi}{2F}\sum_{n=0}^{N-1}\{[1 - \mu(x, y, \phi_n)]\overline{q}'(\gamma_k, \phi_n) + \mu(x, y, \phi_n)\overline{q}'(\gamma_{k+1}, \phi_n)\},$$

where $$\bar{q}'(\gamma_k, \phi_n) = \Delta\gamma \sum_{i=-I/2}^{I/2} \cos\gamma_i q'(\gamma_i, \phi_n) H(k, i) G(k, i), \quad (26)$$

$H(k, i)$ is given by Eq. (16), and $G(k, i)$, which is the discrete form of the function $g(\gamma_0, \gamma)$ in Eq. (12), is given by $$G(k, i) = \left[\frac{\cos\frac{\gamma_k - \gamma_i}{2}}{\cos\frac{\gamma_k + \gamma_i}{2}}\right]^2. \quad (27)$$

The noise properties of the reconstructed images will be considered next. In the presence of noise, the acquired fan-beam sinogram $q(\gamma_i, \beta_n)$ can be treated as a stochastic process. Throughout this description, a bold letter and the corresponding normal letter is used to denote a stochastic process and its mean, respectively. It has been shown that, to a very good approximation, data noise in CT can be treated as an uncorrelated stationary stochastic process. In this situation, the covariances of the measured fan-beam sinogram $q(\gamma_i, \beta_n)$ can be expressed as $$Cov\{q(\gamma_i,\beta_n), q(\gamma_{i'},\beta_{n'})\} = q_0 \delta(\gamma_i - \gamma_{i'}) \delta(\beta_n - \beta_{n'}), \quad (28)$$

where $\delta(.)$ denotes the Kronecker delta function, and $q_0$ is a constant denoting the noise level. Consequently, images reconstructed from and quantities estimated from $q(\gamma_i, \beta_j)$ can also be treated as stochastic processes. Below, we derive image variances obtained with the FFBP, the previous hybrid, and the new hybrid algorithms in their discrete forms.

The noise properties of the FFBP algorithm in discrete form may be considered. Using $q(\gamma_i, \beta_n)$ in Eq. (14), one can reconstruct a stochastic image $a_F(x, y)$. Considering Eqs. (14) and (28), one can show that the variance of $a_F(x, y)$ can be expressed as $$Var\{a_F(x, y)\} = q_0 (\Delta\beta)^2 (\Delta\gamma)^2 \sum_{n=0}^{N} \frac{F^2}{4[L(x, y, \beta_n)]^4} \sum_{i=-I/2}^{I/2} \cos^2\gamma_i$$

$$\times \{[1-\eta(x,y,\beta_n)]H(k,i) + \eta(x,y,\beta_n)H(k+1,i)\}^2, \quad (29)$$

where matrix $H$ is given by Eq. (16), and $k$ and $\eta(x,y,\beta_n)$ are given by Eq. (13).

The noise properties of the previous hybrid algorithm in discrete form may be considered. Because $q(\gamma_i, \beta_n)$ is a stochastic process, its discrete Fourier transform $Q'_m(\gamma_i)$ with respect to $\beta_n$ is also a stochastic process. So is the quantity $\hat{q}'(\gamma_i, \phi_n)$ that is calculated from $Q'_m(\gamma_i)$ by use of Eq. (19). It can be shown that $\hat{q}'(\gamma_i, \phi_n)$ is an uncorrelated stationary stochastic process with $$Cov\{\hat{q}'(\gamma_i,\phi_n), \hat{q}'(\gamma_{i'},\phi_{n'})\} = q_0 \delta(\gamma_i \oplus \gamma_{i'}) \delta(\phi_n - \phi_{n'}). \quad (30)$$

The result of Eq. (30) indicates that $\hat{q}'(\gamma_i, \phi_n)$ is an uncorrelated stationary stochastic process. Consequently, the discrete parallel-beam sinogram $\hat{p}(\xi_k, \phi_n)$ estimated from $\hat{q}'(\gamma_i, \phi_n)$ by use of Eq. (18) should also be interpreted as a stochastic process. So is the filtered version $\bar{p}(\xi_k, \phi_n)$ of the interpolated discrete parallel-beam sinogram $\hat{p}(\xi_k, \phi_n)$ (see Eq. (22)). Therefore, using Eqs. (18), (22), and (30), one can express the covariance $\bar{p}(\xi_k, \phi_n)$ as $$Cov\{\bar{p}(\xi_k, \phi_n), \bar{p}(\xi_{k'}, \phi_{n'})\} = \quad (31)$$

$$q_0 (\Delta\xi)^2 \sum_{i=-I/2}^{I/2} \sum_{i'=-I/2}^{I/2} h(\xi_k - \xi_i) h(\xi_{k'} - \xi_{i'}) \times$$

$$[(2\lambda(\xi_i)^2 - 2\lambda(\xi_i) + 1)\delta(\gamma_I - \gamma_{I'}) + (1 - \lambda(\xi_i))\lambda(\xi_{i'})\delta(\gamma_I - \gamma_{I'+1}) + \lambda(\xi_i)(1 - \lambda(\xi_{i'}))\delta(\gamma_I - \gamma_{I'-1})]\delta(\phi_n - \phi_{n'}),$$

where $\lambda(\xi_i)$ and $I$ are given by Eq. (17).

Using $\bar{p}(\xi_k, \phi_n)$ in Eq. (20), one can reconstruct a stochastic image $a_{PH}(x, y)$. Considering Eqs. (20) and (31), one can show that the variance of $a_{PH}(x, y)$ can be expressed as $$Var\{a_{PH}(x, y)\} = \frac{(\Delta\phi)^2}{4} \sum_{n=0}^{N} \{[1 - \zeta(x, y, \phi_n)]^2 Var\{\bar{p}(\xi_k, \phi_n)\} + \quad (32)$$

$$[\zeta(x, y, \phi_n)]^2 Var\{\bar{p}(\xi_{k+1}, \phi_n)\} +$$

$$2\zeta(x, y, \phi_n)[1 - \zeta(x, y, \phi_n)] Cov\{\bar{p}(\xi_k, \phi_n), \bar{p}(\xi_{k+1}, \phi_n)\}\},$$

where $k$ and $\lambda(x,y,\phi_n)$ are given by Eq. (21), $Var\{\bar{p}(\xi_k,\phi_n)\}$ is the variance of $\{\bar{p}(\xi_k,\phi_n)\}$ that can be obtained by letting $k=k'$ and $n=n'$ in Eq. (31), and $Cov\{\bar{p}(\xi_k,\phi_n) \bar{p}(\xi_{k+1},\phi_n)\}$ can be obtained by letting $k'=k+1$ in Eq. (31).

The noise properties of the new hybrid algorithm in discrete form may be considered next. Because $Q'_m(\gamma_i)$ is a stochastic process, the quantity $q'(\gamma_i, \phi_n)$ that is calculated from $Q'_m(\gamma_i)$ by use of Eq. (24) is also a stochastic process. Again, it can be shown [18] that $q'(\gamma_i, \phi_n)$ is also an uncorrelated stationary stochastic process with $$Cov\{q'(\gamma_i,\phi_n), q'(\gamma_{i'},\phi_{n'})\} = q_0 \delta(\gamma_i - \gamma_{i'}) \delta(\phi_n - \phi_{n'}). \quad (33)$$

Considering Eqs. (25) and (33), one can show that the variance of the reconstructed stochastic image $a_{NH}(x, y)$ can be expressed as $$Var\{a_{NH}(x, y)\} = \quad (34)$$

$$\frac{q_0}{4F^2}(\Delta\gamma)^2(\Delta\phi)^2 \sum_{n=0}^{N} \sum_{i=-I/2}^{I/2} \cos^2\gamma_i \{[1 - \mu(x, y, \phi_n)]H(k, i)G(k, i) +$$

$$\mu(x, y, \phi_n)H(k+1, i)G(k+1, i)\}^2,$$

where matrices $H$ and $G$ are given by Eqs. (16) and (27), respectively, and $k$ and $\mu(x,y,\phi_j)$ are given by Eq. (23).

Quantitative results may be considered next. Computer-simulation studies were conducted to evaluate the FFBP, the previous hybrid, and the new hybrid algorithms and to validate quantitatively the theoretically predicted image variances in Eqs. (29), (32), and (34).

The data was obtained as follows. In the numerical studies, the Shepp-Logan phantom on a 128×128 array of square pixels was used to generate noiseless fan-beam sinograms that simulate data acquired by use of different scanning configurations. A fan-beam sinogram is composed of 180 projection views, each of which contains 257 detector bins. Using such noiseless sinograms as the means, noisy sinograms were generated by adding uncorrelated stationary Gaussian noise. As shown in FIG. 3, a fan-beam scanning configuration can be specified by the focal length F and the center fan angle C. In simulation studies, two fan-beam configurations were considered, one of which is specified by (a) F=363 pixels and C=0.43 π and the other by (b) F=107 pixels and C=0.90π. Configuration (a) represents one that is used in a typical CT scanner, whereas configuration (b) represents one that has the same FOV as that of configuration (a), but has a focal length shorter than that of configuration (a). We first reconstruct images from simulated noiseless and noisy fan-beam sinograms of the Shepp-Logan phantom.

In an attempt to investigate the resolution properties of the FFBP, the previous hybrid, and the new hybrid algorithms, the moduli of Fourier transforms of images reconstructed by use of the three algorithms may be calculated and compared. Such moduli can provide information about the frequency contents of and possible distortions in reconstructed images.

The theoretical predictions for image variances reconstructed by use of the three algorithms in their discrete forms are given by Eqs. (29), (32), and (34). In an attempt to verify the validity of these analytic formulas, empirical variances were calculated from images reconstructed from a large number of statistically independent sets of fan-beam sinograms by use of these algorithms. Specifically, for each of the two configurations (i.e., configurations (a) and (b)), 4000 sets of fan-beam sinograms were generated that contain uncorrelated stationary Gaussian noise. Using each of the three algorithms, 4000 noisy images have been reconstructed, which can be used to calculate the empirical image variances as $$\tilde{V}(x, y) = \frac{1}{M-1} \left\{ \sum_{m=1}^{M} [\tilde{a}_m(x, y)]^2 - \frac{1}{M} \left[ \sum_{m=1}^{M} \tilde{a}_m(x, y) \right]^2 \right\}, \quad (35)$$

where $\tilde{a}_m(x,y)$ denotes the mth image in the total of M (=4000) noisy images reconstructed by use of each of the three algorithms.

Figure 4A:
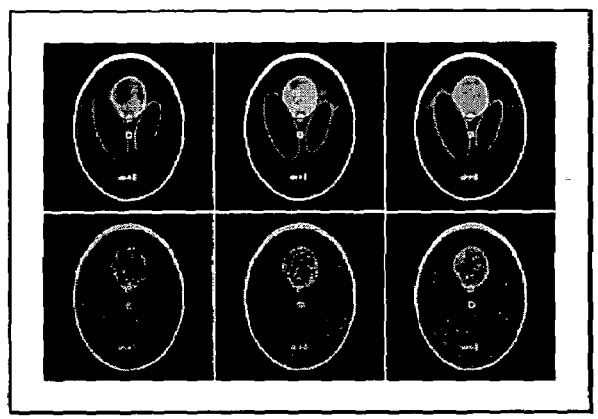
FIG. 4 depicts images reconstructed from fan-beam sinograms.
Figure 4B:
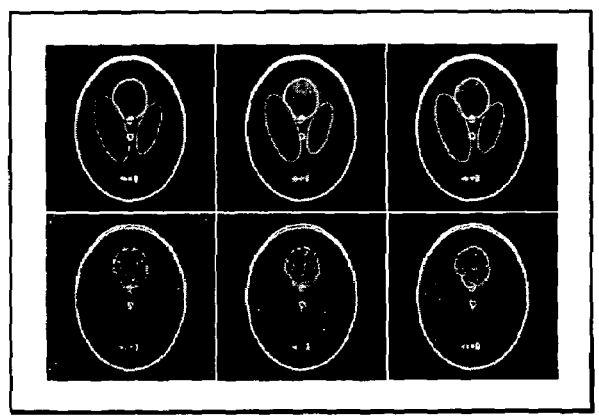

The reconstructed images may be considered next. From fan-beam sinograms of the Shepp-Logan phantom generated with configurations (a) and (b), images may be reconstructed and displayed, as shown in FIGS. 4a and 4b, respectively. Images in the first and second rows were reconstructed from noiseless and noisy sinograms by use of the FFBP (first column), the new hybrid (second column), and the previous hybrid (third column) algorithms, respectively. As shown in FIG. 4a, for configuration (a) with a large F and a small C, images reconstructed by use of the three algorithms appear to be visually similar. However, as shown in FIG. 4b, for configuration (b) with a small F and a large C, the FFBP algorithm amplifies data noise and aliasing artifacts more significantly than do the hybrid algorithms. Images obtained with the new hybrid algorithm appear to have a better resolution than do images obtained with the previous hybrid algorithm because the former can avoid the 1D linear interpolation (see Eq. (18)) that is used in the latter. Results in FIG. 4 also suggest that noise levels in images reconstructed by use of the new hybrid algorithm is more uniform than that in images reconstructed by use of the FFBP and the previous hybrid algorithms. This observation will be verified quantitatively below.

Image resolution will be considered next. In an attempt to compare the resolution properties in images reconstructed by use of the three algorithms, we consider images that contain only point-like structures. Fan-beam sinograms were generated with configurations (a) and (b) from three images each of which contains a single point on pixel (68, 68), (80, 48), and (90, 90), respectively.

Figure 5A:
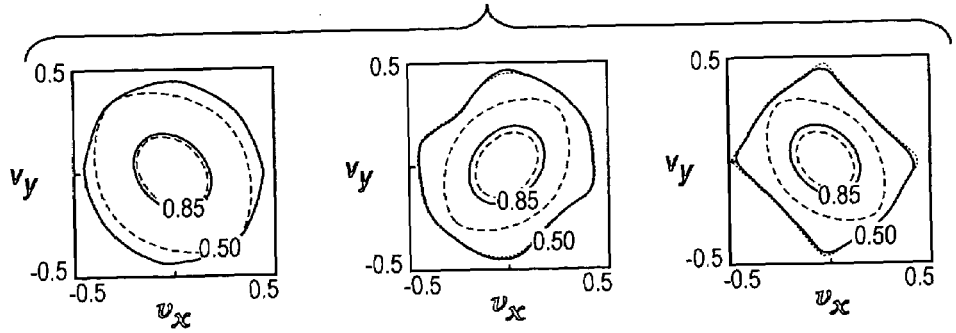
FIG. 5 depicts contours of the moduli of the Fourier transforms that may be used by the system of FIG. 1.
Figure 5B:
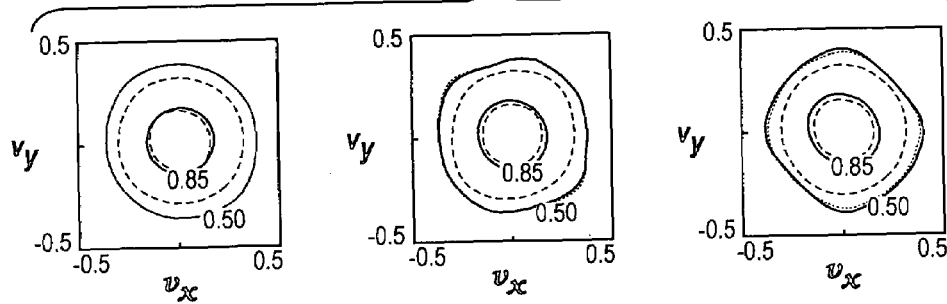
Figure 6A:
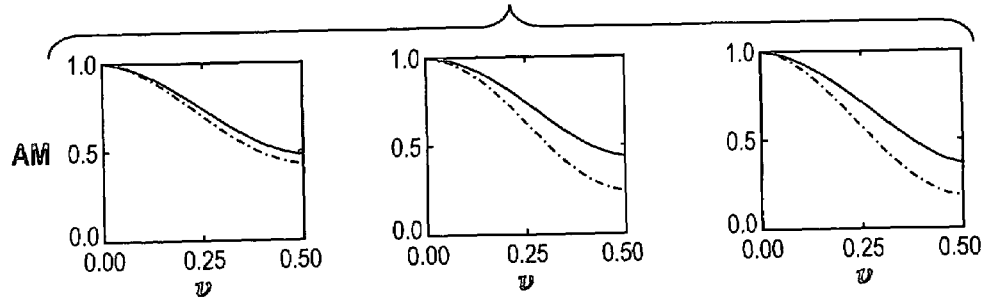
FIG. 6 depicts average moduli of the Fourier transforms of reconstructed images.
Figure 6B:
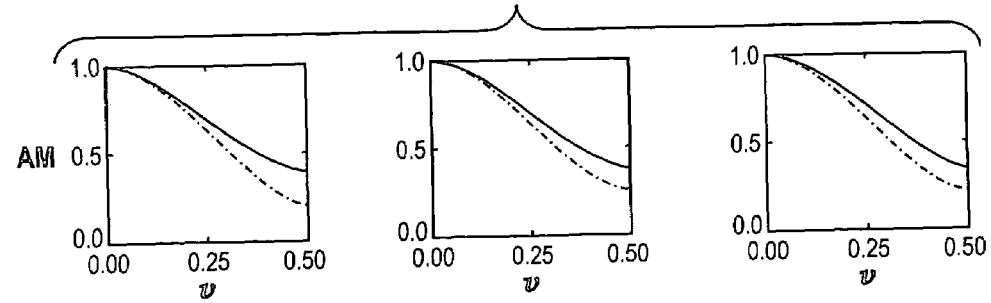

In FIG. 5, the contours of the moduli of the 2D Fourier transforms of the reconstructed points are shown as a functions of spatial frequencies. The first and second rows in FIG. 5 display the results obtained for configurations (a) and (b), respectively. The first, second, and third columns in FIG. 5 display the results obtained for points on pixels (68, 68), (80, 48), and (90, 90) by use of the FFBP (dotted curve), the previous hybrid (dash-dotted), and the new hybrid (solid curve) algorithms, respectively. As shown in FIG. 5, the solid and dotted curves virtually coincide with each other, suggesting that, in the absence of data noise, images reconstructed by use of the new hybrid and the FFBP algorithms have virtually identical frequency contents. It can also be observed that the dash-dotted curves are generally inside the corresponding solid curve, suggesting that the image resolution obtained with the previous hybrid algorithm is inferior to that obtained with the new hybrid algorithm. One can also convert the moduli on 2D Cartesian grids in FIG. 5 onto polar grids and then calculate the average moduli over the polar angles. Such average moduli (AMs) play a role similar to that of the conventional modulation transfer function. FIG. 6 displays such average moduli, which clearly demonstrate that the new hybrid algorithm has a resolution property virtually identical to that of the FFBP algorithm and better than that of the previously hybrid algorithm.

Figure 7A:
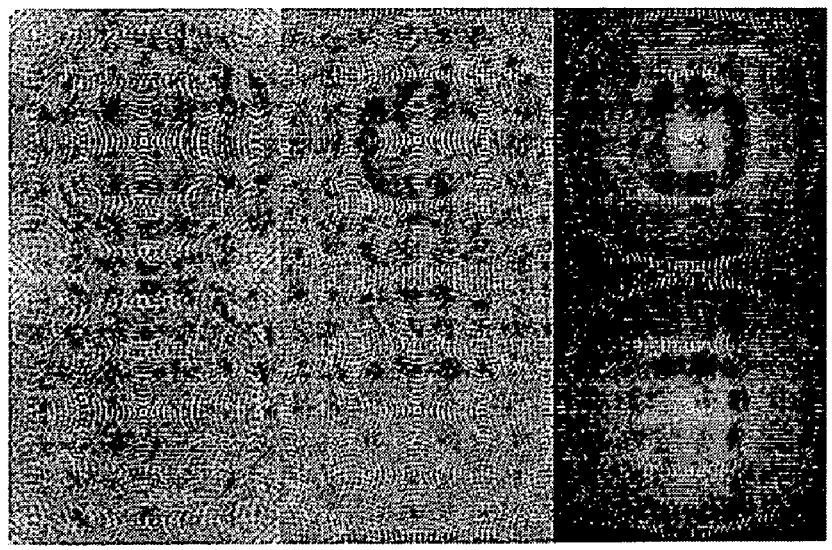
FIG. 7 depicts variance images comparing the FFBP (first column), the new hybrid algorithm (second column) and the previous hybrid algorithm (third column)
Figure 7B:
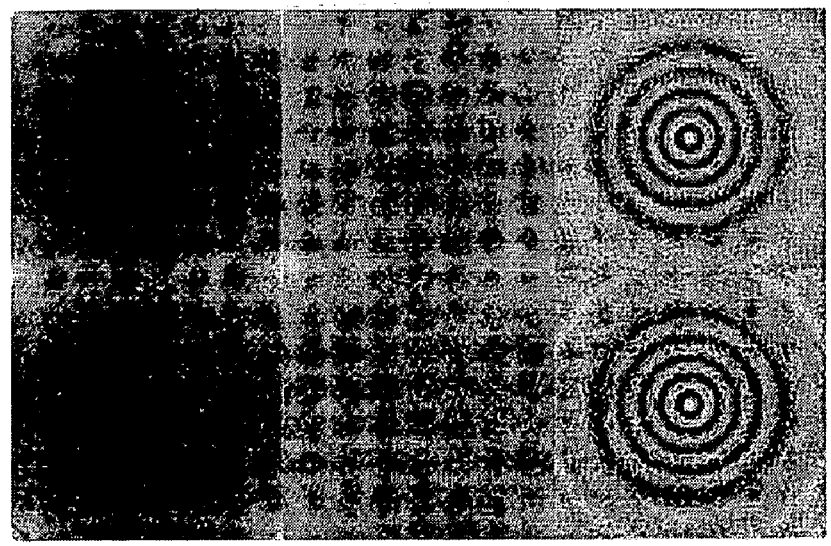

Image variance will be considered next. For each of the two fan-beam configurations, 4000 sets of noisy sinograms were generated from which noisy images were reconstructed by use of each of the three algorithms. Using these reconstructed images in Eq. (35), empirical image variances were computed. The corresponding image variances were also calculated by use of the theoretical formulas in Eqs. (29), (32), and (34) The results displayed in FIGS. 7a and 7b are for configurations (a) and (b), respectively. The first and second rows in FIGS. 7a and 7b display the theoretical and empirical variances obtained by use of the FFBP (first column), the new hybrid (second column), and the previous hybrid (third column) algorithms. In FIG. 8, the profiles of these variance-images are shown on horizontal rows through the image-array centers, which were obtained with the FFBP (dotted), the new hybrid (solid), and the previous hybrid (dash-dotted) algorithms for configurations (a) and (b). The corresponding empirical results obtained with the FFBP (+), the new hybrid (*), and the previous hybrid (Δ) algorithms are also displayed. The empirical results in FIGS. 8 and 9 clearly confirm our theoretical predictions (see Eqs. (29), (32), and (34) for variances in images reconstructed by use of the three algorithms.

Figure 8A:
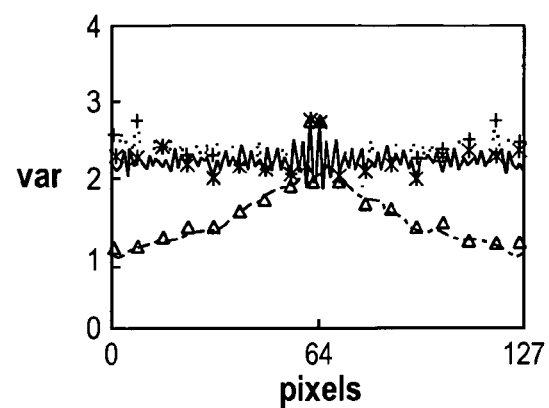
FIG. 8 depicts theoretical profiles on the center rows in variance images.

For configuration (a) with a large F and a small C, as shown in FIGS. 7a and 8a, variances in images reconstructed by use of the FFBP algorithm appear to be generally uniform, except that variances in peripheral regions are slightly higher than those in the inner regions in the image space. On the other hand, variances in images reconstructed by use of the new hybrid algorithm are virtually uniform throughout the image space. Variances in images reconstructed by use of the previous hybrid algorithm are, in general, lower than those obtained with the FFBP and the new hybrid algorithms, reflecting the impact of the 1D linear interpolation in Eq. (18) that converts a discrete fan-beam sinogram to a discrete parallel-beam sinogram. As shown in FIGS. 5 and 6, the reduction of image variances obtained with the previous hybrid algorithm can, however, result in a reduction of image resolution when samples of the fan-beam sinogram are sparse.

Figure 8B:
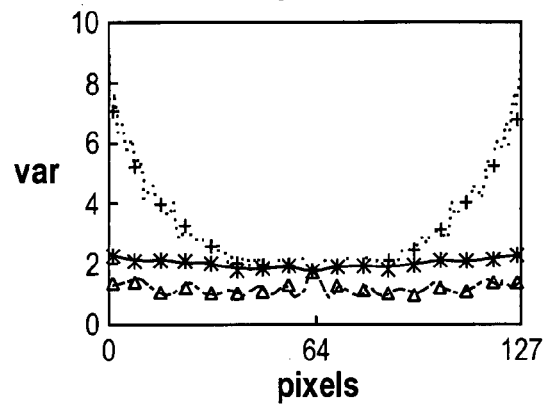

For configuration (b) with a small F and a large C, as shown in FIGS. 7b and 8b, image variances obtained with the FFBP algorithm are highly non-uniform, because, in this situation, the factor L in Eq. (2) can significantly amplify noise and aliasing artifacts in peripheral regions in the image space. In contrast, variances in images reconstructed by use of the new hybrid algorithm remain relatively uniform throughout the image space. Again, variances in images reconstructed by use of the previous hybrid algorithm appear to be non-uniform and are, in general, lower than those obtained with the FFBP and the new hybrid algorithms because of the additional 1D linear interpolation in Eq. (18). However, as shown in FIGS. 5 and 6, such an interpolation can lead to a reduced image resolution when samples of the fan-beam sinogram are sparse.

It is also interesting to observe in FIGS. 7 and 8 that the level and uniformity of image variances obtained with the new hybrid algorithm remain relatively unchanged for the two configurations that have distinctly different focal lengths and center fan angles. However, the level of non-uniformity in variance-images obtained with the FFBP and the previous hybrid algorithms are strongly dependent upon the configuration parameters (e.g., the focal length F). For example, as shown in FIG. 7, variance-images obtained with the previous hybrid algorithm contain prominent ring patterns. For configuration (a), because F is relatively large (as compared to the FOV size), the relationship between $\xi$ and $\gamma$ is close to being linear. Therefore, the linear interpolation in Eq. (18) results in an overall decrease of image variances from the center to the outer regions in the image space. For configuration (b), however, because F is comparable to the FOV size, the non-linearity between $\xi$ and $\gamma$ becomes significant. In this case, the linear interpolation in Eq. (18) leads to oscillating ring structures within the variance-images in FIG. 7.

Figure 9:
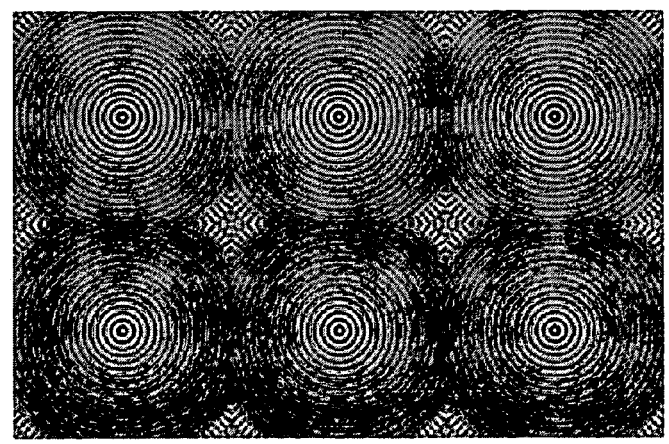
FIG. 9 depicts variance images obtained for a fan-beam configuration.

When the focal length F approaches infinity, the fan-beam configuration approaches the parallel-beam configuration. In this situation, the three algorithms (even in their discrete forms) should yield images with identical properties. Sinograms were generated by use of a fan-beam configuration with a focal length F(=50000 pixels) that is much larger than the FOV size. Therefore, this configuration can, in a practical sense, be regarded as a parallel-beam configuration. From 4000 sets of noisy sinograms generated with this configuration from the Shepp-Logan phantom, images were reconstructed and the empirical image variances were computed from the reconstructed images. For this configuration, Eqs. (29), (32), and (34) were used to calculate the corresponding theoretical image variances. Both theoretical and empirical results of this study are shown in FIG. 9. Again, the theoretical predictions (the first row in FIG. 9) are clearly confirmed by the empirical results (the second row in FIG. 9). Also, as expected, identical image variances were obtained with the FFBP (first column), the new hybrid (second column), and the previous hybrid (third column) algorithms for this configuration. The fine ring structures that appear in FIG. 9 can be attributed to the linear interpolation involved in the backprojection steps (see Eqs. (14), (20), and (25)) in all three algorithms. In fact, such fine structures also appear in forms modulated by the fan-beam effect in the variance-images in FIG. 7. For example, for the previous hybrid algorithm, as the results in the third column in FIG. 7 show, such fine structures are visually overwhelmed by the more significant ring structures introduced by the non-linear relationship between $\xi$ and $\gamma$ and by the linear interpolation in Eq. (18).

Following is a short discussion of the results of this first embodiment. In this work, a new hybrid algorithm for image reconstruction in fan-beam CT has been described. This new algorithm is mathematically equivalent in its continuous form to the FFBP and the previous hybrid algorithms. However, under realistic discrete conditions, the new and existing algorithms respond differently to data noise and aliasing artifacts. Using discrete forms of these algorithms, analytic expressions were derived for noise properties (e.g., image variances) in reconstructed images. Computer-simulation studies were performed to evaluate and compare the resolution and noise properties of the existing and the new algorithms. Both theoretical and numerical results clearly indicate that the new algorithm combines the favorable resolution property of the FFBP algorithm and the favorable noise property of the previous hybrid algorithm while eliminating their shortcomings.

As the theoretical and numerical results demonstrated, one of the highly desirable characteristics of the new hybrid algorithm is that its noise properties are much less dependent upon the scanning configurations than are those of the FFBP and the previous hybrid algorithms. For a given FOV, as the focal length decreases, the noise properties of the new hybrid algorithm remain relatively unchanged, whereas the FFBP algorithm amplifies data noise and aliasing artifacts more significantly, and the previous hybrid algorithm yields variance-images with more conspicuous ring structures. These results may have implications for the design of compact CT systems with reduced focal lengths without sacrificing the FOV sizes. For a compact CT system with a short focal length (e.g., configuration (b)), but an FOV that is the same as that of a typical CT system (e.g., configuration (a)), one can use the new hybrid algorithm to obtain images with improved noise properties over those obtained with the FFBP and the previous hybrid algorithms. Therefore, in terms of noise properties, the new hybrid algorithm has an evident advantage over the FFBP and the previous hybrid algorithms when applied to reconstructing images from data acquired with such compact CT systems. On the other hand, for a fixed focal length, one can enlarge the FOV size by increasing the maximum fan angle. Again, images reconstructed from data acquired with such a system by use of the new hybrid algorithm would have lower noise levels than that in images reconstructed by use of the FFBP algorithm and more uniform noise levels than that found in images reconstructed by use of the previous hybrid algorithm.

As displayed in FIGS. 7 and 8, noise levels in images reconstructed by use of the new hybrid algorithm are much more uniform than those in images reconstructed by use of the FFBP and the previous hybrid algorithm. Such noise uniformity can be desirable for detection/classification tasks that are based upon CT images. Results of the simulation studies validate quantitatively the derived theoretical results for image variances in Eqs. (29), (32), and (34), which not only can provide insights into the algorithms' precision in estimation tasks but also may be used for evaluating their performance by use of statistical/mathematical model observers in detection/classification tasks. Performance assessment of a reconstruction algorithm in a model-observer study generally require knowledge of image variances and covariances. An approximation of such knowledge can be computed empirically from a large number of reconstructed images. However, this computation can be time consuming, and, more importantly, the empirical results so obtained can have significant statistical variations. In contrast, our derived theoretical expressions for image variances and covariances can readily be used in model-observer studies, thus avoiding empirical calculation of image variances and covariances and potential statistical variations within such empirically computed quantities.

Because the new hybrid algorithm calculates a set of shift-variant filtration coefficients (see Eqs. (11) and (25)), it is slightly less efficient computationally than is the previous hybrid algorithm. However, the new hybrid algorithm remains computationally more efficient than the FFBP algorithm. Finally, the new hybrid algorithm can readily be generalized to reconstruction of images from data acquired in the half-scan fan-beam configuration, asymmetric fan-beam configuration, fan-beam configurations with equi-distance detectors, and fan-beam configurations with spatially variant focal lengths.

In another embodiment, half-scan strategy could be used as a means for reducing the scanning time and radiation dose delivered to the patient in fan-beam computed tomography (CT). Also, in helical CT, the data weighting/interpolation functions are often devised based upon half-scan configurations. In half-scan CT, after appropriately normalizing the redundancy in data, the fan-beam filtered-backprojection (FFBP) algorithm can be used for reconstructing images. As discussed above, the FFBP algorithm can be susceptible to data noise and aliasing artifacts, because it invokes a spatially-variant weighting factor that can amplify data noise and sample aliasing. Furthermore, because of the lack of data over the full angular range $2\pi$ in half-scan CT, the FFBP algorithm yields images with highly non-uniform resolution and noise properties throughout the image space. Such non-uniformity of spatial resolution and noise could considerably impede an image's utility in both estimation and detection/classification tasks.

In this embodiment, the algorithm for full scan CT (developed above) has been generalized to reconstruct images in half-scan CT. The resolution and noise properties are investigated in images reconstructed from half-scan data by use of the proposed new half-scan algorithm of this embodiment and half-scan FFBP algorithms. In particular, analytic expressions are derived for image variances and numerical studies are performed to compare empirically the resolution and noise properties in images reconstructed by use of both algorithms. Quantitative results in the numerical studies demonstrate that the proposed algorithm of this embodiment yields images with more uniform spatial resolution and lower and more uniform noise levels than does the half-scan FFBP algorithm. Extensive simulation studies also verify the validity of the derived analytic expressions for image variances. The analytic results on image-noise properties can be used in the calculation of model observers that assess image-quality in detection/classification tasks.

The projection data $q(\gamma,\beta)$ of an object function $\alpha(x,y)$, which are acquired by use of an equi-angular fan-beam CT configuration, as shown in FIG. 3, can be interpreted as a function of projection angle $\beta$ and detector index $\gamma$. In full-scan CT, knowledge of $q(\gamma,\beta)$ is available in the full data space $W=\{|\gamma|\leq\gamma\max, 0\leq\beta<2\pi\}$, where $2\gamma_{max}$ denotes the maximum-fan angle. One can divide the full data space W into four subspaces: A, B, C, and D, where $A=\{|\gamma|\leq\gamma_{max}, 0<\beta\leq 2\gamma_{max}-2\gamma\}$, $B=\{|\gamma|\leq\gamma_{max}, 2\gamma_{max}-2\gamma<\beta\leq\pi-2\gamma\}$, $C=\{|\gamma|\leq\gamma_{max},\pi-2\gamma\leq\beta<\pi+2\gamma_{max}\}$, and $D=\{|\gamma|\leq\gamma_{max},\pi+2\gamma_{max}\leq\beta<2\pi\}$. It can be shown that information about $q(\gamma,\beta)$ in subspace A is identical to that in subspace C and that information about $q(\gamma,\beta)$ in subspace B is identical to that in subspace D. This observation leads to the development of the half-scan CT in which data $q(\gamma,\beta)$ are acquired only within the union space of A, B, and C. Obviously, the half-scan data contain redundant information because information in subspaces A and C is identical. Such a data redundancy can be normalized into the form shown (below) in Eq. (1) of this embodiment, $$q_w(\gamma,\beta)=w(\gamma,\beta)q(\gamma,\beta), \quad (1)$$

where the weighting function $w(\gamma,\beta)$ equals 1 in subspace B and 0 in subspace D and satisfies $w(\gamma,\beta)+w(-\gamma,\beta+2\gamma+\pi)=1$ in subspace A and C.

The conventional half-scan algorithm reconstructs an image directly from the weighted projection $q_w(\gamma,\beta)$ by use of the FFBP algorithm. Below, the full-scan algorithm (discussed above) has been generalized into a form for image reconstruction from $q_w(\gamma,\beta)$.

In this regard, let $p(\xi,\phi)$ denote the parallel-beam projections. It is well known that, when $\phi=\beta+\gamma$ and $\xi=F\sin\gamma$, the parallel-beam projection $p(\xi,\phi)$ is mathematically identical to the fan-beam projection $q(\gamma,\beta)$. For a given $\gamma$, one can apply the Fourier-shift theorem to the weighted projections to obtain the equation, $$q_{wr}(\gamma,\phi) = \frac{1}{2}\sum_{k=-\infty}^{\infty}[e^{-jk\gamma}Q_k^{(w)}(\gamma)+(-1)^k e^{jk\gamma}Q_k^{(w)}(-\gamma)]e^{jk\phi}, \quad (2)$$

where $$Q_k^{(w)}(\gamma) = \frac{1}{2\pi}\int_0^{2\pi}q_w(\gamma,\beta)e^{-jk\beta}d\beta$$

denotes the Fourier series expansion of $q_w(\gamma,\beta)$ with respect to $\beta$. One can interpret $q_{wr}(\gamma,\phi)$ as defining a set of parallel-beam projections. In a discrete case, however, the samples of $q_{wr}(\gamma,\phi)$ on grids uniformly distributed on the $\gamma$-axis are spread non-uniformly on the $\xi$-axis because of the non-linear relationship between $\xi$ and $\gamma$. Therefore, the conventional parallel-beam filtered backprojection (FBP) algorithm has to be modified so that it can be directly applied to samples of $q_{wr}(\gamma,\phi)$ on uniform grids on the y-axis for image reconstruction.

Using $\xi=F\sin\gamma$ and $q_{wr}(\gamma,\phi)$ in the parallel-beam FBP algorithm, one obtains the expression, $$a(x,y) = \int_0^{2\pi}d\phi\int_{-\gamma\max}^{\gamma\max}d\gamma F\cos\gamma q_{wr}(\gamma,\phi)h(F\sin\gamma_0 - F\sin\gamma), \quad (3)$$

where $$h(\xi) = \int_{-\infty}^{\infty}dv|v|e^{j2\pi v\xi}$$

denotes the spatial function of the ramp filter $|v|$, and $\gamma_0$ is determined by the expression $$\gamma_0 = \arcsin\left(\frac{x\cos\phi+y\sin\phi}{F}\right). \quad (4)$$

Using the expression of $h(\xi)$, $\xi_0=F\sin\gamma$, and $\xi=F\sin\gamma$ in Eq. (3) of this embodiment, we obtain the proposed algorithm for image reconstruction from half-scan data as $$a(x,y) = \qquad (5)$$
$$\frac{1}{F}\int_0^{2\pi}d\phi\int_{-\gamma\max}^{\gamma\max}d\gamma\cos\gamma q_{wr}(\gamma,\phi)\left[\frac{\gamma_0-\gamma}{\sin(\gamma_0-\gamma)}\right]^2 h(\gamma_0-\gamma)g(\gamma_0,\gamma),$$

where $$g(\gamma_0, \gamma) = \left[\frac{\cos\frac{\gamma_0 - \gamma}{2}}{\cos\frac{\gamma_0 + \gamma}{2}}\right]^2. \quad (6)$$

The proposed algorithm in Eq. (5) of this embodiment eliminates the undesirable spatially-variant weighting factor in the FFBP algorithm. However, because $g(\gamma_0,\gamma)$ is not a function of $\gamma_0-\gamma$, the filtration in the proposed algorithm of this embodiment (i.e. the integration over $\gamma$ in Eq. (5) of this embodiment)) becomes shift-variant. Therefore, the conventional discrete fast Fourier transform (DFFT) cannot be used to compute the filtration in Eq. (5) of this embodiment. One may, however, use non-uniform DFFT or matrix multiplication techniques to calculate the shift-variant filtration.

Noise properties will be considered next. The half-scan FFBP algorithm and the proposed algorithm (see Eq. (5) of this embodiment) in their continuous forms are mathematically equivalent. In practical situations, however, one must use the algorithms in discrete forms to reconstruct images because the acquired data are discrete in nature. It is in their discrete forms that these algorithms propagate data noise and sample aliasing differently.

The proposed half-scan algorithm of this embodiment in discrete form will be considered next. Assume that there are I+1 detectors at a projection view and that there are N+1 projection views uniformly distributed over $2\pi$. For notational convenience, both I>0 and N>0 are assumed to be even integers. (The results can readily be generalized to situations where I and N are odd integers.) Let $$\Delta\gamma = \frac{2\gamma_{\max}}{I+1}$$

and $\gamma_i = i\Delta\gamma$, where $i=-I/2, -I/2-1, \ldots, I/2-1, I/2$, and let $$\Delta\beta = \frac{2\pi}{N+}$$

and $\beta_n = n\Delta\beta$, where $n=0,1,\ldots,N$. The expression, $q(\gamma_i, \beta_n)$, can be used to denote the discrete data in half-scan CT. Therefore, $q(\gamma_i,\beta_n)=0$ for $\beta_n > \pi + 2\gamma_{max}$. The weighted discrete data is given by the expression, $$qw(\gamma_i,\beta_n) = w(\gamma_i,\beta_n)q(\gamma_i,\beta_n). \quad (7)$$

The discrete form of the reconstruction algorithm depends upon the interpolation scheme that is used in the backprojection step. In the derivation below, we assume that a linear interpolation is invoked in the backprojection step. One can readily use other interpolation schemes to replace the linear interpolation. However, such a change of interpolation schemes would not lead to a fundamental change of the results presented in this embodiment.

Let $$\Delta\phi = \frac{2\pi}{N+1}$$

and $\phi_n = n\Delta\phi$, where $nk=0,1,\ldots,N$. For a given point (x,y) in the image space and a projection angle $\phi_n$, one can calculate the values, $$k = \left[\frac{\gamma_0(x,y,\phi_n)}{\Delta\gamma}\right] \quad (8)$$

$$\mu(x,y,\phi_n) = \frac{\gamma_0(x,y,\phi_n)}{\Delta\gamma} - k,$$

For a given $\gamma_i$, one can calculate the discrete Fourier transform, $Q_m^{(w)}\gamma i)$, of the weighted discrete data $qw(\gamma_i, \beta_n)$ with respect to $\beta_n$. Using $Q_m^{(w)}(\gamma_i)$ a discrete version of $q_{wr}(\gamma,\phi)$ in Eq. (2) of this embodiment can be computed in the form, $$q_{wr}(\gamma_i, \phi_n) = \frac{1}{2}\sum_{m=-N/2}^{N/2} [e^{-jm\gamma_i}Q_m^{(w)}(\gamma_i) + (-1)^m e^{jm\gamma_i}Q_m^{(w)}(-\gamma_i)]e^{jm\phi n}. \quad (9)$$

Substituting the computed $q_{wr}(\gamma_i, \phi n)$ into Eq. (5) of this embodiment, one obtains the integration over $\gamma$ in Eq. (5) in the form, $$\bar{q}_{wr}(\gamma_k, \phi_n) = \Delta\gamma\sum_{i=-I/2}^{I/2}\cos\gamma_i q_{wr}(\gamma_i, \phi_n)H(k, i), \quad (10)$$

where H denotes the filtration matrix with elements defined as $$H(k,i) = \left[\frac{\gamma_k - \gamma_i}{\sin(\gamma_k - \gamma_i)}\right]^2 h(\gamma_k - \gamma_i)\left[\frac{\cos\frac{\gamma_k - \gamma_i}{2}}{\cos\frac{\gamma_k + \gamma_i}{2}}\right]^2. \quad (11)$$

Using Eq. (10) of this embodiment in Eq. (5) of this embodiment and considering a linear interpolation in the backprojection step, the proposed half-scan algorithm can be obtained in its discrete form, $$a(x,y) = \quad (12)$$
$$\frac{\Delta\phi}{F}\sum_{n=0}^{N-1}\{[1-\mu(x,y,\phi_n)]\bar{q}_{wr}(\gamma_k,\phi_n) + \mu(x,y,\phi_n)\bar{q}_{wr}(\gamma_{k+1},\phi_n)\}.$$

Using Eq. (12) of this embodiment, image variances are derived below by use of the proposed algorithm in its discrete form.

The variances in reconstructed images will be considered next. In the presence of noise, the measured data should be treated as a stochastic process. A bold letter and the corresponding normal letter may be used to denote a stochastic process and its mean, respectively. In CT applications, the fan-beam projections $q(\gamma_i, \beta_n)$ are converted from the collected photons on the detectors. The numbers of these photons satisfy the Poisson distribution, and it can be shown that, to a very good approximation, $q(\gamma_i, \beta n)$ can be treated as uncorrelated stochastic processes, i.e., $$Cov\{q(\gamma_i, \beta_n), q(\gamma_{i'}, \beta_{i'})\} = \frac{1}{\sqrt{\rho(\gamma_i, \beta_n)\rho(\gamma_{i'}, \beta_{n'})}} \delta_{ii'}\delta_{nn'}, \quad (13)$$

where $\delta_{ij}$ denotes the Kronecker delta function, and $\rho(\gamma_i, \beta n)$ is the mean number of x-rays on detector (i,n). Therefore, considering Eq. (7) of this embodiment, the normalized data $qw(\gamma_i, \beta n)$ is a stochastic process, with a covariance given by $$Cov\{q_w(\gamma_i, \beta_n), q_w(\gamma_{i'}, \beta_{n'})\} = \frac{\omega(\gamma_i, \beta_n)\omega(\gamma_{i'}, \beta_{n'})}{\sqrt{\rho(\gamma_i, \beta_n)\rho(\gamma_{i'}, \beta_{n'})}} \delta_{ii'}\delta_{nn'}, \quad (14)$$

Consequently, $Q_m^{(w)}(\gamma_i)$ is also a stochastic process because it is the Fourier series expansion coefficient of $qwr(\gamma_i, \beta n)$. So is the quantity $qwr(\gamma_i, \phi n)$ that is calculated from $Q_m^{(w)}(\gamma_i)$. By considering the defining expression, $$\sigma(\gamma_i, \gamma_{i'}, \beta_n, \beta_{n'}) = \frac{\omega(\gamma_i, \beta_n)\omega(\gamma_{i'}, \beta_{i'})}{\sqrt{\rho(\gamma_i, \beta_n)\rho(\gamma_{i'}, \beta_{n'})}}, \quad (15)$$

one can show that $qwr(\gamma_i, \phi n)$ can be interpreted approximately as an uncorrelated stochastic process with a covariance given by $$Cov\{q_{wr}(\gamma_i, \phi_n), q_{wr}(\gamma_{i'}, \phi_{n'})\} \approx \frac{1}{4}[\bar{\sigma}(\gamma_i, \gamma_{i'}) + \bar{\sigma}(-\gamma_i, -\gamma_{i'})]\delta_{ii'}\delta_{nn'}, \quad (16)$$

where $\bar{\sigma}(\gamma_i, \gamma y_i')$ is an approximation of $\sigma(\gamma_i, \gamma_i', \beta n, \beta_{n'})$ by assuming that it is a function independent of $\beta$.

Finally, using Eqs. (9), (12), and (16) of this embodiment, the variances in images reconstructed by use of the proposed algorithm in its discrete form may be obtained in the form, $$Var\{a(x,y)\} \approx \quad (17)$$

$$\frac{1}{4F^2}(\Delta\gamma)^2(\Delta\phi)^2 \sum_{n=0}^{N} \sum_{i=-I/2}^{I/2} \cos^2\gamma_i [\bar{\sigma}(\gamma_i, \gamma_{i'}) + \bar{\sigma}(-\gamma_i, -\gamma_{i'})] \times$$

$$\{[1 - \mu(x, y, \phi_n)]H(k, i) + \mu(x, y, \phi_n)H(k+1, i)\}^2$$

where k and $\mu(x,y,\phi_j)$ are given by Eq. (8) of this embodiment, and matrix H is given by Eq. (11) of this embodiment. We have previously derived image variances obtained with the FFBP algorithm in its discrete form. Because the half-scan algorithm reconstructs an image directly from the normalized fan-beam projections in Eq. (1) of this embodiment by use of the FFBP algorithm, the expression for image variances obtained with the half-scan FFBP algorithm is essentially identical to that for image variances obtained with the full-scan FFBP algorithm. Although such an expression is not given here, it was used to compute image variances for comparison with the empirical image variances obtained in our numerical studies below.

The results of this study will be considered next. Computer-simulation studies were performed to evaluate the numerical properties of the proposed and half-scan FFBP algorithms. In an attempt to reveal the possible asymmetric resolution and noise properties in images obtained with the half-scan reconstruction algorithms, a bead phantom (as defined in Table 1) and a thorax/shoulder phantom were for assessment of the algorithm performance. (The thorax/shoulder phantom corresponds to a 2D slice at z=150 mm within the 3D thorax/shoulder phantom that is available at the website: http://www.imp.uni-erlangen.de.)

TABLE 1

Parameters for the bead phantom, ($x_0$, $y_0$) and radius are in unit of half of the FOM size.]

| | ($x_0$, $y_0$) | radius | intensity |
|---|---|---|---|
| 1 | (0, 0) | 0.9 | 1.0 |
| 2 | (0, 0) | 0.7 | 1.2 |
| 3 | (0, 0) | 0.08 | 2.0 |
| 4-7 | (±0.566, ±0.566) | 0.08 | 2.0 |
| 8 | (−0.8, 0) | 0.08 | 2.0 |
| 9 | (0, −0.8) | 0.08 | 2.0 |
| 10 | (0.8, 0) | 0.08 | 2.0 |
| 11 | (0, 0.8) | 0.08 | 2.0 |
| 12-15 | (±0.8, ±0.8) | 0.08 | 2.0 |

Both phantoms were used to generate noiseless and noisy fan-beam data. Images with sizes of 300×300 mm² are represented as 512×512 arrays of square pixels. Image properties not only are algorithm-dependent, but also rely upon configuration parameters such as focal lengths and maximum-fan angles. In our numerical studies, we generated different fan-beam data by use of two fan-beam configurations specified by (a) F=850 mm and $\gamma_{max}$=0.09π and by (b) F=250 mm and $\gamma_{max}$0.34π, respectively. Parameter set (a) specifies a configuration that has large focal length and small maximum-fan angle, whereas parameter set (b) defines a configuration that has a field of measurement (FOM) as big as that in configuration (a), but has a much smaller focal length and/or larger maximum-fan angle. A fan-beam data set is composed of 1024 projections uniformly distributed over 2π, each of which contains 1201 detector bins. Noisy data were obtained by computing the logarithm of the ratio between the entrance fluence and detected fluence. The entrance fluence per detector was assumed to be 1.5×10⁵. The collected fluence by each detector is assumed to follow the Poisson statistics with a mean that is the product of the entrance fluence and the exponential of the negative fan-beam projection. The redundant information in the half-scan data was normalized by use of the weighting function proposed by Parker, which is given by the expression, $$\omega(\gamma, \beta) = \begin{cases} \sin^2\left(\frac{\pi}{4}\frac{\beta}{\gamma_m - \gamma}\right) & (\gamma, \beta) \in A \\ 1 & (\gamma, \beta) \in B \\ \sin^2\left(\frac{\pi}{4}\frac{\pi + 2\gamma_m - \beta}{\gamma_m + \gamma}\right) & (\gamma, \beta) \in C \\ 0 & (\gamma, \beta) \in D \end{cases} \quad (18)$$

Reconstructed images may be considered next. In FIGS. 10a and 10b, images are shown of the bead phantom reconstructed from half-scan data acquired with configurations (a) and (b), respectively. Images in the first and second rows were reconstructed from noiseless and noisy data, respectively, by use of the FFBP algorithm (the left column) and the proposed algorithm (the right column). For data acquired with configuration (a), as shown in FIG. 10a, both algorithms reconstruct noiseless images with visually identical quality. But, in the presence of noise, the half-scan FFBP algorithm yields a slightly noisier image than does the proposed algorithm of this embodiment. In contrast, for configuration (b), the lower-left region in the image reconstructed from noiseless data by use of the half-scan FFBP algorithm appears to be slightly inferior to that in the image reconstructed by use of the proposed algorithm of this embodiment. More prominently, in the presence of noise, the half-scan FFBP algorithm yields considerably noisier images than does the proposed algorithm of this embodiment. One can see that there are many streak artifacts in both images, which are caused by the high attenuation paths along those beads. It is interesting to observe that the appearance of these streak artifacts are very different in the images obtained by the two algorithms. In particular, in the lower and left regions of the image obtained with the half-scan FFBP algorithm, the streak artifacts and data noise have been amplified much more significantly than those in the upper and right regions, which makes the structures in the lower and left regions very noisy. Conversely, such highly non-uniform amplification of data noise and the streak artifacts does not appear in images reconstructed by use of the proposed algorithm.

FIG. 11a and FIG. 11b also display images reconstructed by use of the two algorithms from noisy half-scan data of the thorax/shoulder phantom acquired with configurations (a) and (b), respectively. Observations and conclusions similar to those for the bead phantom discussed above can be made. In an attempt to demonstrate the noise properties of reconstructed images, FIG. 12 shows the same images as those in FIG. 11, but with a much narrower display window of [−100HU, 200HU].

Resolution properties may be considered next. Quantitative evaluation for the resolution properties of the half-scan FFBP algorithm and the proposed algorithm of this embodiment were also conducted. Specifically, phantoms were used that consist of point-like structures to generate fan-beam data and reconstruct images from that data. From these reconstructed images, the moduli of their Fourier transforms were calculated. To facilitate an effective comparison of resolution properties throughout the image space, a figure of merit may be introduced and used to refer to as the areas under the average moduli (AAM). The AAM may be obtained by (1) converting the Fourier moduli on the two-dimensional Cartesian grids to polar grids, (2) calculating the average modui over the polar angles, and (3) computing the areas under these one-dimensional average moduli. In FIG. 13, we display spatial locations on the two diagonal lines at which the AAMs are calculated.

In FIG. 14, the AAMs obtained by use of the half-scan FFBP algorithm and the proposed algorithm were plotted as functions of locations on the two diagonal lines. It can be observed in FIG. 14a that, for configuration (a), images obtained by use of the two algorithms have comparable resolution properties except that the resolution property of the half-scan FFBP algorithm is slightly less uniform. In contrast, for configuration (b), as FIG. 14b demonstrates, the resolution properties of the half-scan FFBP algorithm become highly non-uniform, whereas the resolution properties of the proposed algorithm remain virtually uniform. It should be pointed out that the seemingly high values of AAM in FIG. 14b obtained with the half-scan FFBP algorithm do not imply a high resolution. Instead, such high values can be attributed to the strong artifacts in images obtained with the half-scan FFBP algorithm. In FIG. 15, the contour plots of the Fourier transform moduli of the reconstructed point-like structures are shown at (I) (−102 mm, −102 mm) and (II) (102 mm, 102 mm). Clearly, the highly non-circular contours suggest that, for the configuration (b), the half-scan FFBP algorithm yields images with more significant distortions than does the proposed algorithm.

Noise properties will be considered next. The analytic expression for image variances obtained with the proposed algorithm in its discrete form is given by Eq. (17) of this embodiment. An expression was also derived for image variances obtained by use of the half-scan FFBP algorithm in its discrete form, which highly resembles the expression in Eq. (30) in the previous embodiment and is thus not given here. Using these analytic expressions, we calculated the image variances for configurations (a) and (b). In an attempt to verify the validity of these theoretical results, we use a circular water phantom with a radius of 150 mm to generate 4000 statistically independent sets of noisy fan-beam data. Each set of data is obtained by assuming an entrance fluence of $2.5 \times 10^5$. Using the two algorithms, we reconstructed 4000 noisy images, which are subsequently used for computing empirically image variances. We display in FIGS. 16a and 16b theoretically predicted (top row) and empirically computed (bottom row) image variances for configurations (a) and (b), respectively. The results obtained with the half-scan FFBP algorithm and the proposed algorithm are shown in the left and right columns, respectively. Additionally, in FIG. 17, profiles of these image variances are displayed on their central-horizontal rows. These results clearly indicate that the theoretical and empirical results agree with each other, confirming the validity of the theoretical predictions of image variances. They also demonstrate that the proposed algorithm generally yields images with lower and more uniform noise levels than does the half-scan FFBP algorithm. The cause of the half-scan FFBP algorithm reconstructing images with highly non-uniform noise levels can be attributable to the combination of the spatially-variant weighting factor in its backprojection and the lack of data at certain views in a half-scan configuration. For example, for the half-scan configurations considered, it can be shown that, for projection views around the lower-left region in the image space, the spatially-variant factor is generally larger than 1 in the lower-left region and smaller than 1 in the upper-right region of the image space, thus resulting in significant amplification and suppression of noise in these regions, respectively. This amplification-suppression phenomena can be observed in image-variance results, as shown in FIGS. 16 and 17. It can be mentioned in passing that the decreasing image-variances toward the peripheral regions of the FOV in FIGS. 16 and 17 obtained with the proposed algorithm reflect the property of Poisson statistics of the projection data. For Poisson data, the variances are determined by their means. For the used water phantom, these means are higher in the center portion of the detector array at each projection view, consequently leading to the higher variances in the inner region of the image space. We have also performed analytic and numerical studies by use of data containing uncorrelated stationary Gaussian noise. These results, which are not shown here, demonstrated that, although the half-scan FFBP algorithm still produces images with highly non-uniform noise properties, the proposed algorithm yields images with uniform noise properties.

In half-scan fan-beam CT, the existing FFBP-based algorithm can lead to images with highly non-uniform resolution and noise properties in situations where the focal lengths are small relative to the size of the FOM and/or the maximum-fan angles are large. In this embodiment, an algorithm has been described for image reconstruction in half-scan fan-beam CT. Theoretical analysis and numerical studies suggest that the proposed algorithm yields images with more uniform resolution property and lower and more uniform noise levels than does the half-scan FFBP algorithm. Analytic expressions have been derived for image variances obtained by use of the half-scan FFBP and the proposed algorithms in their discrete forms and verified the validity of these expressions by use of numerical studies. The proposed algorithm would be particularly useful for image reconstruction from data acquired by use of configurations with short focal lengths and/or large maximum-fan angles, which may be encountered in compact micro-CT and radiation therapeutic CT applications. The derived analytic expressions for the image-noise properties can be used for image-quality assessment in detection/classification tasks by use of model-observers. The proposed algorithm can also be generalized to other scanning configurations such as fan-beam configurations with an off-set detector, spatially varying focal lengths, or equispace detectors. The strategy discussed here may also be applied to reconstructing images from data acquired with cone-beam configurations.

In another embodiment, it is know that cone-beam data acquired with a circular orbit has insufficient information for exact 3D reconstruction. In an attempt to obtain sufficient data sets, non-planar and non-circular acquisition orbits in addition to the circular orbit have been investigated. Exact algorithms have been developed for image reconstruction from cone-beam data acquired with non-circular and non-circular obits. Despite this, the cone-beam scanning configuration with a circular orbit remains one of the most popular configurations and has been widely employed for data acquisition in, e.g., micro-CT and in CT imaging in radiation therapy because of its minimal mechanical complexity. The Feldkamp-Davis-Kress (FDK) algorithm, which is a 3D generalization of the conventional 2D fan-beam filtered backprojection (FFBP) algorithm, was developed for reconstructing 3D images from cone-beam data acquired with a circular orbit. Other algorithms such as the T-FDK algorithm have also been proposed for improving image quality over those obtained with the FDK algorithm.

In the FDK algorithm, the spatially-variant weighting factor can not only increase the computational load, but also amplify data noise and aliasing artifacts, especially in situations where the focal lengths are comparable to the size of field of measurement (FOM). It has been shown that the weighting factor can be eliminated by rebinning the cone-beam data into parallel beam data. However, the rebinning interpolations may lead to a loss of spatial resolution when cone-beam data samples are sparse. Through the use of a Fourier rebinning scheme and a spatially shift-variant filtration scheme, the algorithm described in previous embodiments can eliminate the weighting factor in the FFBP algorithm and avoid an explicit interpolation. Numerical results have demonstrated that the algorithm can improve the noise properties without compromising the spatial resolution in reconstructed images. Motivated by these observations for the above described 2D algorithm, a circular orbit algorithm is presented in this embodiment with spatially shift-variant filtration for image reconstruction from cone-beam data acquired with a circular orbit. To a certain extent, the algorithm resembles conceptually the T-FDK algorithm in that both entail the conversion of the cone-beam data into parallel fan-beam data and reconstruction from such converted data. However, because the new algorithm uses the Fourier shift theorem to achieve the data conversion and a spatially shift-variant filtration in reconstruction, it can avoid the explicit interpolations involved in the T-FDK algorithm. Computer simulation studies have been performed to compare the proposed, FDK and T-FDK algorithms. Numerical results of these studies demonstrate that the proposed algorithm has resolution comparable to and noise properties that are better than the FDK algorithm. As compared to the T-FDK algorithm, the proposed algorithm reconstructs images with an improved in-plane resolution.

The theory of the FDK algorithm will be considered first. Let f(x,y,z) denote the spatial function to be reconstructed, and let q(s,b,β) denote the cone-beam data acquired with a 2D flat-panel detector and a circular source orbit of a radius of F, where β∈[0,2π] is the projection angle and (s,b) are the coordinates of a rotating coordinate system on a virtual detector plane containing the center of rotation and mapped from the real flat-panel detector with maximum sizes of $2s_m$, and $2b_m$ along radial and vertical directions, respectively. The FDK algorithm can be expressed as shown below.

$$f_{FDK}(x, y, z) = \int_0^{2\pi} d\beta \frac{1}{U^2} \int_{-s_m}^{s_m} ds\, h(s_o' - s) \frac{F}{\sqrt{F^2 + s^2 + b^2}} q(s, b_o, \beta) \quad (1)$$

where $$s_o'(x, y, \beta) = \frac{F(x\cos\beta + y\sin\beta)}{F + x\sin\beta - y\cos\beta}, \quad (2)$$

$$b_o(x, y, z, \beta) = \frac{zF}{F + x\sin\beta - y\cos\beta}, \quad (3)$$

$$U(x, y, \beta) = \frac{F + x\sin\beta - y\cos\beta}{F} \quad (4)$$

As discussed above, the spatially-variant weighting factor U can significantly amplify data noise and aliasing artifacts when the focal length F is comparable to the size of the FOM.

The proposed algorithm will be considered next. As shown in FIG. 18, (only half space z≧0 is shown), the cone-beam data acquired from a circular orbit can be rebinned into fan-beam data that are vertically parallel to each other. Similar to the situation in 2D fan-beam configuration, the cone-beam rotation angle β and the rotation angle of the rebinned vertically-parallel fan-beam projections satisfy the equation that follows.

$$\phi = \beta + \arctan(s/F) \quad (5)$$

Therefore, using the Fourier-shift theorem and Eq. (5) of this embodiment, one can obtain the vertically-parallel fan-beam data from the measured circular-orbit cone-beam data in the form, $$p(s, b, \phi) = \sum_{k=-\infty}^{\infty} e^{jk(\phi - \arctan(s/F))} Q_k(s, b), \quad (6)$$

where $Q_k(s,b)$ denotes the Fourier series expansion of the con-beam data q(s,b,β) with respect to β. Notice that, for these rebinned data, except for those in the mid-plane, no two rays corresponding to the same row of detectors are parallel to each other. Instead, if mapping the rebinned data of the same row to the virtual detector plane containing the center of rotation, one obtains a curved trajectory. Let u denote the height of this trajectory, which can be expressed as a function of s and b, i.e., $$u = \frac{F^2}{(F^2 + s^2)} b \qquad (7)$$

Therefore, one can express the data function in the {s,u} space as $$p(s, u, \phi) = \tilde{p}\left(s, \frac{u(F^2 + s^2)}{F^2}, \phi\right). \qquad (8)$$

Although p(s,u,φ) represents parallel-beam projections, it is not uniformly sampled over s. Letting $$\xi = \frac{sF}{\sqrt{s^2 + F^2}} \text{ and } \xi_o = \frac{s_o F}{\sqrt{s_o^2 + F^2}}, \qquad (9)$$

one can show that $$h(\xi_o - \xi) = \left(\frac{s_o - s}{\frac{F_{s_o}}{\sqrt{F^2 + s_o^2}} - \frac{F_s}{\sqrt{F^2 + s^2}}}\right)^2 h(s_o - s). \qquad (10)$$

Finally, using the results above, the new circular orbit algorithm can be obtained which is given as follows.

$$f(x, y, z) = \qquad (11)$$
$$\frac{1}{2}\int_0^{2\pi} d\phi \int_{-s_m}^{s_m} ds \cos\gamma \, p(s, u_o\phi) G(s_o, s) h(s_o - s) \left(\frac{F}{\sqrt{(s^2 + F^2)}}\right)^3,$$

where $$\cos\gamma = \frac{F^2}{\sqrt{F^4 + u^2(s^2 + F^2)}} \qquad (12)$$

accounts for the effect of cone-beam open angle γ along the rotation axis, $$G(s_0, s) = \left(\frac{s_o - s}{\frac{F_{s_o}}{\sqrt{F^2 + s_o^2}} - \frac{F_s}{\sqrt{F^2 + s^2}}}\right)^2, \qquad (13)$$

$$s_o(x, y, \phi) = \frac{F(x\cos\phi + y\sin\phi)}{\sqrt{F^2 - (x\cos\phi + y\sin\phi)^2}}, \qquad (14)$$

and $$u_o(x, y, z, \phi) = \frac{z\sqrt{F^2 - (x\cos\phi + y\sin\phi)^2}}{\sqrt{F^2 - (x\cos\phi + y\sin\phi)^2} + x\sin\phi - y\cos\phi}. \qquad (15)$$

It can be seen that the original FDK algorithm involves a shift-invariant filtration over s, whereas the proposed algorithm invokes a shift-variant filtration because G(s$_0$,s) (in Eq. (13) of this embodiment) is not a function of s$_0$–s However, the most important feature of the new algorithm is that it eliminates the weighting factor U and thus improves the noise properties without sacrificing the in-plane spatial resolution.

Furthermore, previous results indicated that image intensities obtained by use of the FDK algorithm decrease as one moves away from the mid-plane. As the results below show, both the T-FDK algorithm and the algorithm proposed in this embodiment can compensate for such an intensity drop. Additionally, if we remove the cone-angle weighting factor cos γ in Eq. (11) of this embodiment, an even better improvement can be obtained. This algorithm, which can be referred to as "the proposed algorithm without cone-angle weighting", suggests that the missing data problem can be compensated for by adjusting the preweighting factor in the proposed algorithm.

The results will be discussed next. Computer simulation studies were performed for comparison and evaluation of the FDK algorithm, the T-FDK algorithm, and the proposed algorithm. In these studies, a numerical 3D Shepp-Logan phantom represented by a 256$^3$ matrix was used. The physical length of each side of the volume was assumed to be 300 mm. The projection data was assumed to be acquired by use of a flat panel detector rotating on a circular-orbit with a focal length F=455 mm, s$_m$×b$_m$=262.5×262.5 mm$^2$, and the maximum cone angle is thus +/−30°. The detector panel is subdivided into 257×257 bins. The cone-beam data were generated over 360 projection views uniformly distributed over 2π.

In FIG. 19, images for a 2D slice are displayed at y=−37.5 mm reconstructed by use of the FDK algorithm (upper left), the T-FDK algorithm (upper right), the proposed algorithm (lower left), and the proposed algorithm without cone-angle weighting (lower right), respectively. All images are shown in a gray-scale window [0,60HU]. The corresponding profiles along z direction at the position x=0 mm are shown in FIG. 20. Because the profiles obtained from the T-FDK algorithm and the proposed algorithm are close to each other, only a single curve is shown for the two algorithms. From these results, it can be seen that the intensity drop with increasing cone-angle in the FDK algorithm can be substantially compensated for by the use of the T-FDK algorithm and the proposed algorithm. Additionally, as shown in these results, the proposed algorithm without cone-angle weighting appears to outperform the other algorithms under study.

In an attempt to evaluate quantitatively the algorithms' resolution properties, cone-beam data was first generated from a point-source phantom containing two small spheres and then images were reconstructed from the cone-beam data. The two small spheres with radii of 0.75 mm, located at (0 mm, 37.5 mm, 0 mm) and (0 mm, 37.5 mm, 37.5 mm), respectively, in the field of view. Using the reconstructed images for slices at z=0 mm and z=37.5 mm, their 2D Fourier transformations were calculated and subsequently the 2D moduli of these Fourier transforms were calculated. Such moduli provide quantitative information about the frequency contents (i.e., resolution properties) in reconstructed images.

By normalizing these moduli to their maxima and averaging over polar angles in the 2D Fourier space, one can obtain single profiles as a function of spatial frequency, which is referred to as the average moduli in the Fourier transform (AMFT). (The quantity AMFT plays a role similar to that of the modulation transfer function (MTF) that is widely used for evaluation of the resolution of a linear shift-invariant system.) The AMFTs shown in FIGS. 21a and 21b were computed for the slices at (a) z=0 mm and (b) z=37.5 mm, respectively. The dotted, dashed, and solid curves show the results obtained by use of the FDK algorithm, the T-FDK algorithm, and the proposed algorithm, respectively. These results clearly demonstrate that for both slices, AMFT curves obtained with the FDK and proposed algorithms are virtually identical and are higher than that obtained with the T-FDK algorithm, suggesting that the T-FDK algorithm has a resolution property inferior to that of the FDK algorithm and that the proposed algorithm retains the favorable resolution properties of the FDK algorithm.

The image noise properties of the three algorithms were also investigated. Using a set of noiseless cone-beam projections as the means, 1000 sets of noisy projections were generated by addition of stationary Gaussian noise. From the reconstructed noisy images, empirical image variances were calculated. In the first and second rows of FIG. 22, the 2D variance-images are displayed at z=0 mm and z=37.5 mm, respectively, obtained by use of the FDK algorithm (left), the T-FDK algorithm (middle), and the proposed algorithm (right). In FIGS. 23a and 23b, the profiles are shown along the center columns of the variance-images in the first and second rows of FIG. 22, respectively. It can be seen that, the FDK algorithm amplifies data noise in the peripheral region more significantly than do the other two algorithms. As discussed above, such a noise amplification can be attributable to the spatially-variant weight factor U. The noise level obtained with the proposed algorithm appears to be higher than that obtained with the T-FDK algorithm. This is because the T-FDK algorithm involves additional interpolation operations that can reduce image noise levels. However, such a noise reduction is obtained at the price of compromising the image resolution.

In this embodiment an algorithm has been proposed for image reconstruction from cone-beam data acquired over a circular orbit. This algorithm eliminates the spatially-variant weighting factor in the FDK algorithm by the use of a Fourier rebinning scheme and spatially shift-variant filtration. It resembles the T-FDK algorithm, but can avoid the interpolation operations involved in the latter. Simulation studies have been conducted for quantitative evaluation and comparison of the proposed algorithm, the FDK algorithm, and the T-FDK algorithm in terms of reconstruction accuracy, spatial resolution, and noise properties. Numerical results in these studies clearly demonstrate that the proposed algorithm is more accurate than is the FDK algorithm. It yields images with noise levels lower than the noise levels in images obtained with the FDK algorithm while retaining the favorable resolution properties of the FDK algorithm. The proposed algorithm has a resolution property superior to that of the T-FDK algorithm.

In another embodiment, asymmetric cone-beam CT can be used for increasing the size of the field of measurement (FOM) in micro-CT or in megavoltage CT for patient localization in radiation therapy. From the data acquired with such configuration, images can be reconstructed by use of the conventional FDK algorithm with data weighted by a smooth weighting function. With the increase of the FOM size, however, the FDK algorithm may significantly amplify data noise and aliasing artifacts because it involves a spatially-variant weighting factor. In this embodiment an asymmetric cone-beam algorithm is proposed to reconstruct images from asymmetric cone-beam data. This algorithm eliminates the spatially-variant weighting factor involved in the FDK algorithm, and thus reconstructs images with improved noise properties. It maintains the image spatial resolution by use of a shift-variant filtration scheme to avoid interpolation along the radial direction. Additionally, the proposed algorithm can compensate for the intensity-drop effect resulting from the missing data problem in the FDK algorithm. This algorithm is particularly robust when applied to asymmetric cone-beam CT with large size of FOM and/or small focal angles.

Let $q_\alpha(s,b,\beta)$ denote the cone-beam data acquired with a displaced 2-D flat-panel detector and a circular source trajectory with a radius of F, where $\beta \in [0, 2\pi)$ is the projection angle, and (s, b) are the coordinates of a rotating coordinate system which represents a virtual detector plane containing the center of rotation (COR), as shown in FIG. 24. Suppose that the detector is displaced such that the cone-beam data exist only when $S \in [-s_o, s_m]$. One can weight the acquired data by use of a smooth weighting function $\omega$, which equals 0 for $s \in [-s_m, s_o]$, 1 for $s \in (s_o, s_m]$, and satisfies $\omega(s) + \omega(-s) = 1$ for $S \in [-s_o, s_o]$. The weighted cone-beam data can be expressed as $q_\omega(s,b,\beta) = q_\alpha(s,b,\beta)\omega(s)$. In this embodiment, the prior art weighting function shown below may be used.

$$\omega(s) = \frac{1}{2}\left[\sin\left(\frac{\pi \arctan\frac{s}{F}}{2\arctan\frac{s_o}{F}}\right) + 1\right], s \in [-s_o, s_o]. \quad (1)$$

The algorithm described in this embodiment converts the weighted cone-beam data to vertically parallel fan-beam data by use of the Fourier-shift theorem, which may be shown as:

$$\tilde{p}(s, b, \phi) = \sum_{k=-\infty}^{\infty} e^{jk(\phi - \arctan(s/F))} Q_k(s, b), \quad (2)$$

where $\phi$ denotes the rotation angle of the rebinned vertically parallel fan-beam projections and $Q_k(s,b)$ the Fourier series expansion of the weighted data $q_\omega(s,b,\beta)$ with respect to $\beta$. A data function $p(s,u,\phi)$ is calculated as follows:

$$p(s, u, \phi) = \tilde{p}\left(s, \frac{u(F^2 + s^2)}{F^2}, \phi\right), \quad (3)$$

which accomplishes the mapping of data on the virtual detector along a straight line.

Using this result in the FBP formula for parallel-beam and applying the pre-weighting factor that accounts for the cone angle γ, one can obtain a new asymmetric cone-beam algorithm as follows:

$$f(x, y, z) = \int_0^{2\pi} d\phi \int_{-s_m}^{s_m} ds \cos\gamma p(s, u_o, \phi) \quad (4)$$

$$\left( \frac{s' - s}{\frac{FS'}{\sqrt{F^2 + s'^2}} - \frac{FS}{\sqrt{F^2 + s^2}}} \right)^2 h(s' - s) \left( \frac{F}{\sqrt{s^2 + F^2}} \right)^3.$$

To evaluate the algorithm proposed in this embodiment, computer simulations may be performed to compare images reconstructed by use of the FDK algorithm and the proposed algorithm, both using the weighting function in Eq. (1) of this embodiment. A large cone-angle was used to demonstrate the effect of the proposed algorithm and the FDK algorithm. The low contrast 3D Shepp-Logan phantom (in a cubic volume with side length of 300 mm) was used to generate the projection data with an asymmetric configuration, which has a focal length F=283.2 mm, virtual detector size $S_m = b_m = 337.5$ mm with a displaced side length $s_o = 84.4$ mm (corresponding to maximum cone angles of 50° and −17°), 257×257 detector bins and 360 views over 2π. Images are displayed in FIG. 25(a) for 2D slices at y=−37.5 mm (first column), z=0 mm (second column), z=18.8 mm (third column), and z=37.5 mm (fourth column) in the Shepp-Logan phantom. The first, second and third rows show the corresponding slices in the original phantom, the images reconstructed by use of the FDK algorithm and the images reconstructed by use of the proposed algorithm, respectively. Display window was set to [0,60HU]. FIG. 25(b) also shows the profiles along the center column (z direction) in the first column of FIG. 25(a). It can be seen that the intensity drop with the increase of cone-angle in the FDK algoithm has been significantly compensated for by the proposed algorithm, therefore, the reconstructed area is enlarged along the vertical direction.

To investigate the noise properties of the proposed algorithm and the FDK algorithm quantitatively, empirical variances were calculated from images reconstructed with the two algorithms from 1000 sets of asymmetric cone-beam data that contain uncorrelated noise. The data were generated by use of a sphere water phantom with a radius of 150 mm. The noise data were added by computing the logarithm of the ratio between the entrance fluence and detected fluence. The entrance fluence per detector was assumed to be $1.5 \times 10^5$. The detected fluence at each detector for each detector for each projection was assumed to follow the Poisson statistics for which the mean value was calculated from the exponential attenuation of the entrance fluence. In the first and second rows of FIG. 26(a) the 2D variance-images are displayed at z=0 mm and z=37.5 mm, respectively, obtained by use of the FDK algorithm (left) and the proposed algorithm (right). In FIG. 26(b-c), the profiles are shown along the diagonal lines of the variance-images in the first and second rows of FIG. 26(a), respectively. One can see that the variances of the images reconstructed by use of the FDK algorithm are much higher than those obtained by use of the proposed algorithm, especially in the peripheral regions of the FOM. In order to demonstrate the influence of this difference, a bead phantom was constructed with structures in the peripheral regions. Asymmetric cone-beam data were generated with the configuration described above, noise was added by assuming the entrance fluence per detector to be $1.0 \times 10^4$. FIG. 27 shows the reconstructed images by use of the FDK algorithm (upper row) and the proposed algorithm (lower row) for 2D slices at z=0 mm (left column) and z=37.5 mm (right column). One can observe that the images reconstructed by use of the proposed algorithm is not as noisy as those obtained by use of the FDK algorithm, especially in the peripheral regions of the FOM.

An asymmetric cone-beam algorithm has been described herein for image reconstruction from cone-beam data acquired with an asymmetric configuration. This algorithm improves the noise properties of the conventional FD algorithm, which amplifies data nose and aliasing artifacts significantly when large size of the FOM in the asymmetric configuration is intended. A shift-variant filtration scheme is applied under the proposed algorithm to avoid interpolation so that the spatial resolution is not sacrificed. The proposed algorithm also compensates for the intensity-drop problem in the FDK algorithm, thus increasing the application reconstruction regions.

In another embodiment, Micro-CT is an important tool in biomedical research owing to its capability for noninvasively imaging normal and diseased biology and for monitoring disease progress and response to therapy or genetic modifications. Spatial resolution is one of the most important considerations in micro-CT design. Investigators have proposed to improve the image resolution by the use of a small source-to-subject distance (SSD) to increase magnification of the subject under study onto the detector arrays. As a result, improved spatial resolution can be achieved without decreasing the size of the detection element.

FIG. 28(a) shows a typical scanning configuration with an object completely covered by the x-ray beam. One can move the object closer to the focal spot by reducing the SSD, as shown in FIG. 28(b). This can lead to a better sampling resolution and consequently a better image resolution. In this situation, however, the minimal SSD is determined by the maximum fan-angle and the object size.

The configuration with asymmetric detector has been proposed for increasing the size of field of view (FOV). In this embodiment, we show that it can also be exploited for further improvement of the sampling resolution and thus the image resolution. As shown in FIG. 28(c), a half of the object is now outside of the x-ray beam coverage. In this situation, one can observe in FIG. 28(c) that the distance between the center of the FOV (i.e., the object) and the focal spot is smaller than the SSD in FIG. 28(b), thus allowing further improvement on sampling and image resolution.

Obviously, one needs to use interpolations to convert the data acquired by use of the configuration in FIG. 28(c) into the format so that the conventional fan-beam filtered backprojection (FFBP) algorithm can be applied. However, such interpolations can significantly compromise the potential gain of image resolution by use of the configuration in FIG. 28(c). Additionally, when the FFBP algorithm is applied to data acquired with a configuration with a large maximum fan-beam angle, as in FIG. 28(c), it can yield images with considerable noise and aliasing artifacts.

In this work, instead of using the configuration in FIG. 28(c) for increasing the size of FOV, we propose to utilize it for improving the sampling and image resolution. Moreover, a new reconstruction algorithm has been developed that can reconstruct images directly from the data measured by use of the configuration in FIG. 28(c). Because the resolution enhancement algorithm of this embodiment invokes no additional interpolation for data conversion, it can produce images with the highest spatial resolution allowable by a fan-beam configuration with a fixed maximum fan-angle.

The methods used will be discussed first. The term q(s,β) may be used to denote the data acquired with the configuration shown in FIG. 28(*c*) in which the center of rotation (COR) (i.e., the center of the FOV) is located on the line connecting the focal point and one end of the actual detector, where β∈[0,2π] is the projection-view angle, and s∈[0, 2$s_m$] denotes positions on a virtual detector that passes through the COR and is parallel to the actual detector. The focal length F is defined as the distance between the focal spot and the COR. In FIG. 28(*c*), an axis is plotted, denoted as s', across the COR and perpendicular to the line connecting the focal spot and the COR. Now the configuration in FIG. 28(*c*) can be interpreted as a fan-beam configuration that has a virtual detector that is parallel to the s' axis. The relationship between s' and s is given by $$s' = \frac{sF}{F\cos\gamma_m - (s - s_m)\tan\gamma_m}, \quad (1)$$

where $\gamma_m$ is a half of the maximum fan-angle of the x-ray beam. Using this relationship, one can convert the data q(s,β) that are measured by use of the actual detector onto the grids on the virtual detector (i.e., s'). Subsequently, one can use the FFBP algorithm to reconstruct images from the converted data.

However, in discrete situations discussed above, such a data-conversion involves generally interpolations, which can substantially compromise the image resolution that may potentially be gained by use of the asymmetric configuration. In this embodiment, a reconstruction algorithm is proposed that can reconstruct images directly from the measured data, thus eliminating the otherwise necessary data interpolations and retaining the gain of sampling resolution provided by use of the asymmetric configuration in FIG. 28(*c*). Mathematically, this new algorithm is given by $$f(x, y) = \int_0^{2\pi} d\phi \int_0^{2s_m} ds\, q_r(s, \phi) \times G(s_0, s) h(s_0 - s) J_1(s) J_2(s), \quad (2)$$

where $$q_r(s, \phi) = \frac{1}{2\pi} \sum_{m=-\infty}^{\infty} e^{jm(\phi - \arctan(s'/F))} \times \int_0^{2\pi} d\beta\, q(s, \beta) e^{-jm\beta}, \quad (3)$$

G is defined as $$G(s_0, s) = \left( \frac{s_0 - s}{\frac{s_0' F}{\sqrt{F^2 + s_o'^2}} - \frac{s' F}{\sqrt{F^2 + s'^2}}} \right)^2, \quad (4)$$

and the two Jacobi terms are given by $$J_1(s) = \frac{F^3}{(F^2 + s'^2)^{3/2}}, \quad (5)$$

and $$J_2(s) = \frac{1}{\cos\gamma_m \cdot (\cos\gamma_m - s\tan\gamma_m / F)^2}, \quad (6)$$

respectively.

The results will be considered next. Computer-simulation studies were conducted to demonstrate and compare the performance of the FFBP and proposed algorithms on image-resolution recovery. In these studies, the three configurations shown in FIG. 28 were considered, in which the detector size is 92.5 mm and the distances between the detector and the focal spot is 80 mm. However, the focal lengths for configuration (a), (b), and (c) are F=45 mm, 30 mm, and 17 mm, respectively. The FOV sizes are all 30 mm in the three configurations. The phantom that were used is composed of several sets of bar patterns with different widths, among which the width for the finest bar structures is 0.75 pixel. Three sets of data were generated for the three configurations, each of which consists of 600 detector bins and 720 views evenly distributed over 2π. Images reconstructed from these data by use of the FFBP and proposed algorithms are displayed in FIG. 29. For a more quantitative comparison, FIG. 30 displays the reconstructed profiles of the thinnest bar patterns. As these results show, the proposed algorithm yields images comparable to or better than that obtained with the FFBP algorithm. In particular, for configuration (c), it can be observed that the proposed algorithm significantly outperforms the FFBP algorithm.

A strategy has been proposed in this embodiment for significantly enhancing image resolution without altering the hardware (i.e., the detector, the source, and the relative configurations between the detector and source.) In particular, a completely asymmetric fan-beam configuration has been described for achieving the highest possible sampling and image resolution. Furthermore, an algorithm has been developed for image reconstruction directly from the measured data. This algorithm yields images with improved resolution over that in images obtained with the FFBP algorithm and is less susceptible to data noise than is the FFBP algorithm. It should be emphasized that the proposed strategy and algorithm can also be applied to cone-beam micro-CT system.

While a preferred embodiment of the present invention has been illustrated and described, it will be understood that changes and modifications may be made therein without departing from the invention in its broader aspects.

The invention claimed is:

1. A method of reconstructing a tomographic image from fan-beam or cone beam data, such method comprising the steps of:
    collecting fan-beam or cone-beam data;
    converting the fan-beam to parallel-beam data with respect to a rotation angle or converting the cone-beam data to parallel fan-beam data;
    performing a shift variant filtration of the parallel-beam data or the parallel fan-beam data to avoid interpolation of the parallel-beam data or parallel fan-beam data; and converting the processed data to images through backprojection or other means.

2. The method of reconstructing the tomographic image as in claim 1 further comprising reconstructing an image from the filtered parallel-beam data using a filtered backprojection algorithm.

3. The method of reconstructing the tomographic image as in claim 1 further comprising defining the fan-beam or cone-beam data as half-scan fan beam data.

4. The method of reconstructing the tomographic image as in claim 1 further comprising defining the fan-beam data as helical-scan data.

5. The method of reconstructing the tomographic image as in claim 1 further comprising defining the fan-beam or cone-beam data as data collected from an object that is offset within the data space.

6. The method of reconstructing the tomographic image as in claim 1 further comprising performing a Fourier expansion on the data with respect to a rotation angle.

7. The method of reconstructing the tomographic image as in claim 6 further comprising linearly shifting the transformed data.

8. The method of reconstructing the tomographic image as in claim 7 further comprising performing an inverse Fourier transform on the shifted data.

9. An apparatus for reconstructing a tomographic image from fan-beam or cone beam data, such apparatus comprising:
means for collecting fan-beam or cone-beam data;
means for converting the fan-beam to parallel-beam data with respect to a rotation angle or cone-beam data to parallel fan-beam data;
means for performing a shift variant filtration of the parallel-beam data or the parallel fan-beam data to avoid interpolation of the parallel-beam data or parallel fan-beam data; and
means for conversion of the processed data to images through backprojection or other means.

10. The apparatus for reconstructing the tomographic image as in claim 9 further comprising means for reconstructing an image from the filtered parallel-beam data using a filtered backprojection algorithm.

11. The apparatus for reconstructing the tomographic image as in claim 9 further comprising defining the fan-beam or cone-beam data as half-scan fan beam data.

12. The apparatus for reconstructing the tomographic image as in claim 9 further comprising defining the fan-beam as helical-scan data.

13. The apparatus for reconstructing the tomographic image as in claim 9 further comprising defining the fan-beam or cone-beam data as data collected from an object that is offset within the data space.

14. The apparatus for reconstructing the tomographic image as in claim 9 further comprising means for performing a Fourier expansion on the data with respect to a rotation angle.

15. The apparatus for reconstructing the tomographic image as in claim 14 further comprising means for linearly shifting the transformed data.

16. The apparatus for reconstructing the tomographic image as in claim 15 further comprising means for performing an inverse Fourier transform on the shifted data.

17. The apparatus for reconstructing the tomographic image as in claim 15 wherein the fourier processor further performs an inverse Fourier transform on the shifted data.

18. The apparatus for reconstructing a tomographic image as in claim 17 wherein the first cosine function further comprises the cosine of a reference angle minus a detector angle divided by two.

19. The apparatus for reconstructing a tomographic image as in claim 18 wherein the second cosine function further comprises the cosine of a reference angle plus a detector angle divided by two.

20. An apparatus for reconstructing a tomographic image from fan-beam or cone beam data, such apparatus comprising:
a sampling system configured to collect fan-beam or cone-beam data;
a fourier processor configured to convert the fan-beam or cone-beam data to parallel-beam data with respect to a rotation angle or the cone-beam data to parallel fan-beam data;
a shift variant filter configured to perform a linear shift of the parallel-beam data or parallel fan-beam data to avoid interpolation of the parallel-beam data or parallel fan-beam data; and
a reconstruction processor configured to convert of the processed data to images through backprojection or other means.

21. The apparatus for reconstructing the tomographic image as in claim 20 wherein the reconstruction processor further comprising a software application for reconstructing an image from the filtered parallel-beam data using a filtered backprojection algorithm.

22. The apparatus for reconstructing the tomographic image as in claim 20 further comprising defining the fan-beam or cone-beam data as half-scan fan beam data.

23. The apparatus for reconstructing the tomographic image as in claim 20 further comprising defining the fan-beam or cone-beam data as helical-scan data.

24. The apparatus for reconstructing the tomographic image as in claim 20 further comprising defining the fan-beam or cone-beam data as data collected from an object that is offset within the data space.

25. The apparatus for reconstructing the tomographic image as in claim 20 wherein the fourier processor further performs a Fourier expansion on the data with respect to a rotation angle.

26. A method of reconstructing a tomographic image from data acquired with a fan beam configuration with constant or spatial variant focal lengths, such method comprising the steps of:
performing a fast Fourier transform on the fan beam data with respect to a set of view angles;
forming a linear combination of complementary data elements of the transformed data, lying at complementary projection angles;
filtering the linear combination of complementary data elements in the spatial domain to avoid interpolation of the linear combination; and
reconstructing an image from the filtered linear combination of complementary data elements using a filtered backprojection algorithm.

27. The method of reconstructing a tomographic image as in claim 26 wherein the step of filtering further comprises using shift variant filtration.

28. The method of reconstructing a tomographic image as in claim 27 wherein the step of reconstructing an image from the filtered linear combination of complementary data elements using a filtered backprojection algorithm further comprises multiplying an integral of a rotation angle by one over a value equal to two times a focal length.

29. The method of reconstructing a tomographic image as in claim 26 wherein the step of filtering further comprises multiplying the linear combination of complimentary data elements by a squared trigonometric function.

30. The method of reconstructing a tomographic image as in claim 29 wherein the squared trigonometric function further comprises a first cosine function divided by a second cosine function.

31. The method of reconstructing a tomographic image as in claim 30 wherein the first cosine function further comprises the cosine of a reference angle minus a detector angle divided by two.

32. The method of reconstructing a tomographic image as in claim 30 wherein the second cosine function further comprises the cosine of a reference angle plus a detector angle divided by two.

33. An apparatus for reconstructing a tomographic image from data acquired with a fan beam configuration with constant or spatial variant focal lengths, such apparatus comprising:
  means for performing a fast Fourier transform on the fan beam data with respect to a set of view angles;
  means for forming a linear combination of complementary data elements of the transformed data, lying at complementary projection angles;
  means for filtering the linear combination of complementary data elements in the spatial domain to avoid interpolation of the linear combination; and
  means for reconstructing an image from the filtered linear combination of complementary data elements using a filtered backprojection algorithm.

34. The apparatus for reconstructing a tomographic image as in claim 33 wherein the means for filtering further comprises means for using shift variant filtration.

35. The apparatus for reconstructing a tomographic image as in claim 33 wherein the apparatus for filtering further comprises apparatus for multiplying the linear combination of complimentary data elements by a squared trigonometric function.

36. The apparatus for reconstructing a tomographic image as in claim 35 wherein the squared trigonometric function further comprises a first cosine function divided by a second cosine function.

37. The apparatus for reconstructing a tomographic image as in claim 33 wherein the means for reconstructing an image from the filtered linear combination of complementary data elements using a filtered backprojection algorithm further comprises means for multiplying an integral of a rotation angle by one over a value equal to two times a focal length.

38. An apparatus for reconstructing a tomographic image from data acquired with a fan beam configuration with constant or spatial variant focal lengths, such apparatus comprising:
  a Fourier processor configured to perform a fast Fourier transform on the fan beam data with respect to a set of view angles;
  a combination processor configured to form a linear combination of complementary data elements of the transformed data, lying at complementary projection angles;
  a spatial filter configured to filter the linear combination of complementary data elements in the spatial domain to avoid interpolation of the linear combination; and
  a reconstruction processor configured to reconstruct an image from the filtered linear combination of complementary data elements using a filtered backprojection algorithm.

39. The apparatus for reconstructing a tomographic image as in claim 38 wherein the spatial filter further comprises a shift variant filter.

40. The apparatus for reconstructing a tomographic image as in claim 38 wherein the filter further comprises a squared trigonometric function.

41. The apparatus for reconstructing a tomographic image as in claim 40 wherein the squared trigonometric function further comprises a first cosine function divided by a second cosine function.

42. The apparatus for reconstructing a tomographic image as in claim 41 wherein the first cosine function further comprises the cosine of a reference angle minus a detector angle divided by two.

43. The apparatus for reconstructing a tomographic image as in claim 42 wherein the second cosine function further comprises the cosine of a reference angle plus a detector angle divided by two.

44. The apparatus for reconstructing a tomographic image as in claim 38 wherein the reconstruction processor further comprises an arithmetic processor adapted to multiply an integral of a rotation angle by one over a value equal to two times a focal length.

* * * * *